(12) United States Patent
i Tormo et al.

(10) Patent No.: US 11,974,063 B2
(45) Date of Patent: Apr. 30, 2024

(54) RELIABLY CONVEYING TRANSCRIBED TEXT AND PHYSIOLOGICAL DATA OF A REMOTE VIDEOCONFERENCE PARTY SEPARATELY FROM VIDEO DATA

(71) Applicant: KOA HEALTH DIGITAL SOLUTIONS S.L.U., Barcelona (ES)

(72) Inventors: Albert Garcia i Tormo, Barcelona (ES); Nicola Hemmings, Bristol (GB); Aleksandar Matic, Lloret de Mar (ES); Johan Lantz, Barcelona (ES)

(73) Assignee: KOA HEALTH DIGITAL SOLUTIONS S.L.U., Barcelona (ES)

( * ) Notice: Subject to any disclaimer, the term of this patent is extended or adjusted under 35 U.S.C. 154(b) by 0 days.

(21) Appl. No.: 17/875,308

(22) Filed: Jul. 27, 2022

(65) Prior Publication Data

US 2023/0247169 A1    Aug. 3, 2023

Related U.S. Application Data

(63) Continuation-in-part of application No. 17/680,168, filed on Feb. 24, 2022.

(30) Foreign Application Priority Data

Jan. 31, 2022   (EP) .................................. 22154300

(51) Int. Cl.
*H04N 5/278* (2006.01)
*A61B 3/11* (2006.01)
(Continued)

(52) U.S. Cl.
CPC .......... *H04N 5/278* (2013.01); *A61B 5/0022* (2013.01); *A61B 5/0205* (2013.01); *G10L 15/26* (2013.01);
(Continued)

(58) Field of Classification Search
CPC .... H04N 5/278; A61B 5/0022; A61B 5/0205; A61B 3/112; A61B 5/02405;
(Continued)

(56) References Cited

U.S. PATENT DOCUMENTS 8,441,356 B1 *   5/2013  Tedesco ............. G08B 21/0453
                                                                     340/539.15
10,579,742 B1 *  3/2020  Fernandez ............. G10L 15/16
(Continued)

FOREIGN PATENT DOCUMENTS

JP        2020256391 A     11/2010

OTHER PUBLICATIONS

European Search Report dated Jun. 14, 2023, from the European Patent Office in the related European Application EP22204422 (2 pages).

(Continued)

*Primary Examiner* — Stella L. Woo
(74) *Attorney, Agent, or Firm* — MARSHALL, GERSTEIN & BORUN LLP

(57) ABSTRACT

Transcribed text and physiological data of a remote video conference participant are transmitted to a local device separately from the video data, which depicts the remote party during a time interval. An image of the video data is captured at a time instant within the time interval. A value of a remote party feature is determined remotely using the video data. The remote party feature can be the remote party's heart rate at the time instant. The value of the feature is received onto the local device. Audio data captures sounds spoken by the remote party and is converted by the remote device into words of text. The audio data converted into a particular word was captured at the time instant. The particular word is received onto the local device. The particular (Continued)

word and the value of the feature are displayed in association with one another on the local device.

14 Claims, 14 Drawing Sheets

(51) Int. Cl.
*A61B 5/00* (2006.01)
*A61B 5/0205* (2006.01)
*A61B 5/024* (2006.01)
*A61B 5/08* (2006.01)
*G10L 15/26* (2006.01)
*G16H 80/00* (2018.01)

(52) U.S. Cl.
CPC ............. *G16H 80/00* (2018.01); *A61B 3/112* (2013.01); *A61B 5/02405* (2013.01); *A61B 5/02416* (2013.01); *A61B 5/0816* (2013.01)

(58) Field of Classification Search
CPC ... A61B 5/02416; A61B 5/0816; G10L 15/26; G16H 80/00
USPC ..................................................... 348/14.03
See application file for complete search history.

(56) References Cited

U.S. PATENT DOCUMENTS

| | | | |
|---|---|---|---|
| 2009/0319268 A1 | 12/2009 | Aumont et al. | G10L 15/00 704/236 |
| 2014/0278423 A1 | 9/2014 | Dellisanti et al. | G10L 25/60 |
| 2019/0180871 A1* | 6/2019 | Doerflinger | G16H 50/20 |
| 2020/0265854 A1* | 8/2020 | Moon | H04R 3/00 |
| 2022/0086393 A1* | 3/2022 | Peters | H04N 7/152 |

OTHER PUBLICATIONS

European Search Report dated Jul. 21, 2022, from the European Patent Office in the related European Application EP22154300. 2 (9 pages).

* cited by examiner

TIME-DOMAIN PPG
CALCULATION OF HEART RATE

RELIABLY CONVEYING TRANSCRIBED TEXT AND PHYSIOLOGICAL DATA OF A REMOTE VIDEOCONFERENCE PARTY SEPARATELY FROM VIDEO DATA

CROSS REFERENCE TO RELATED APPLICATION

This application is a continuation in part of, and claims priority under 35 U.S.C. § 120 from, nonprovisional U.S. patent application Ser. No. 17/680,168 entitled "Monitoring Call Quality of a Video Conference to Indicate Whether Speech Was Intelligibly Received," filed on Feb. 24, 2022. Application Ser. No. 17/680,168, in turn, claims the benefit under 35 U.S.C. § 119 from European Patent Application No. EP 22154300.2, filed on Jan. 31, 2022, in the European Patent Office. The subject matter of each of the foregoing documents is incorporated herein by reference.

TECHNICAL FIELD

The present invention relates to a system and method for monitoring the quality of video conferences and more particularly to reliably conveying, separately from interruptible video data, transcribed text along with concurrent physiological data relating to the remote video conference participant.

BACKGROUND

In recent years, remote communication technologies have increasingly gained popularity, a process especially fueled by the recent COVID-19 pandemic and the associated restrictions, such as the requirement to work remotely. Videoconferencing technologies, however, have been hampered by connectivity problems and the loss of transmitted information. This has resulted in sub-optimal call quality, especially in the professional environment, which has often rendered participants of video conferences unable to determine whether the other participants have satisfactorily understood the speaker.

In the context of telehealth, mental health therapy sessions can now be performed through video conferences between health professionals and their patients. However, conventional videoconferencing technologies provide no feedback to the health professionals regarding whether their speech is being properly reproduced to the patient at the remote end.

A system is sought that enables the health professional to monitor the intelligibility of the content that is reproduced at the receiver side for the patient. Based on this information, the health professional can better anticipate comprehension deficiencies by the patient and might even decide to repeat portions of the therapy content that were not understood.

However, in order to administer an effective mental health therapy, the psychiatrist must perceive more than just whether the patient has acoustically understood the psychiatrist's words. The psychiatrist or mental health professional must also be able to evaluate changes in the patient's mental and emotional state in response to the stimulus of the therapy, often by observing the patient's physiological condition. Observing and evaluating the patient's emotional and physiological state is difficult in a remote therapy session, especially if the quality of the audio and video channels degrades.

Thus, a system is sought that not only monitors the quality of the health professional's speech that is reproduced for the remote patient, but also that provides the health professional in real time with an indication of the changes in the patient's physiological condition during the telehealth therapy session.

SUMMARY

The intelligibility of a video conference is monitored using speech-to-text conversion and by comparing the text as spoken to the text that is converted from received audio. A first portion of audio data of speech of a user which is timestamped with a first time is input into a first audio and text analyzer. A second portion of the audio data, which is also timestamped with the first time, is received onto a remote audio and text analyzer. The first audio and text analyzer converts the first portion of audio data into a first text fragment. The remote audio and text analyzer converts the second portion of audio data into a second text fragment. The first audio and text analyzer receives the second text fragment. The first text fragment is compared to the second text fragment. Whether the first text fragment matches the second text fragment is indicated to the user on a display.

A method for monitoring call quality in a video conference uses speech-to-text conversion to compare text fragments as spoken by a first user to corresponding text fragments converted from audio data as received by a remote second user. An audio signal containing encoded audio data of speech of the first user is received onto a first audio and text analyzer. A first portion of the encoded audio data is timestamped with a first time. The audio signal containing the encoded audio data is also received onto a remote audio and text analyzer as presented to the second user. The encoded audio data received onto the remote audio and text analyzer includes a second portion of the encoded audio data that is also timestamped with the first time. The first audio and text analyzer converts the first portion of the encoded audio data into a first fragment of text. The remote audio and text analyzer converts the second portion of the encoded audio data into a second fragment of text. The first audio and text analyzer receives the second fragment of text. The first fragment of text is compared to the second fragment of text. Whether the first fragment of text exactly matches the second fragment of text is indicated to the first user on a graphical user interface. For example, the indicating whether the first fragment of text exactly matches the second fragment of text includes indicating that a word of the first fragment of text is missing from the second fragment of text.

In one implementation, the first user is a mental health professional who is delivering a mental health treatment session to a patient, the second user. The method indicates whether the speech of the mental health professional is being intelligibly received by the patient.

In another embodiment of a method for monitoring call quality, call quality of a video conference is monitored using speech-to-text conversion to compare text fragments as spoken by a remote second user to corresponding text fragments converted from audio data as received by a first user. An audio signal containing encoded audio data representing the speech of the remote second user is received from a remote audio and text analyzer. A first portion of the encoded audio data is timestamped with a first time and is converted into a first fragment of text. A second portion of the encoded audio data, which is also timestamped with the first time, is converted by the remote audio and text analyzer into a second fragment of text. The second fragment of text is received from the remote audio and text analyzer. The first fragment of text is compared to the second fragment of text. A system for monitoring call quality indicates on a graphical user interface whether the first fragment of text converted from audio data as received by the first user exactly matches the second fragment of text converted remotely from audio data as spoken by the second user. In one implementation, the first user is a physician who is providing a mental health therapy to a patient, the second user. The method indicates whether the physician is intelligibly receiving the speech of the patient.

In another embodiment of a method for monitoring call quality, the video quality of video conference is monitored by comparing patterns that are recognized in the video signal as generated and as remotely received. A video signal containing digital image data is received onto a first image recognition system. A first portion of the digital image data is timestamped with a first time. The video signal containing the digital image data is received onto a remote image recognition system. The digital image data received onto the remote image recognition system includes a second portion of the digital image data that is also timestamped with the first time. The first image recognition system recognizes a first pattern in the first portion of the digital image data. The remote image recognition system recognizes a second pattern in the second portion of the digital image data. The first image recognition system receives the recognized second pattern. The recognized first pattern is compared to the recognized second pattern. A system for monitoring video quality of a video conference indicates on a graphical user interface whether the recognized first pattern matches the recognized second pattern. In one implementation, the first pattern is a number that is incremented with each successive digital image of the video signal. The indicating whether the recognized first pattern matches the recognized second pattern includes indicating whether the number formed by the first pattern equals a number that is recognized by the remote image recognition system to be formed by the second pattern.

Yet another embodiment of a method for monitoring the quality of communication between two devices involves converting the input received at the first device into first and second sequences of information, wherein the second sequence includes a first piece of information extracted from the input, sending the first sequence to the second device, which receives the first sequence as a third sequence, extracting a second piece of information from the third sequence to generate a fourth sequence, comparing the first piece of information from the second sequence to the second piece of information from the fourth sequence to detect any deviations between the two, and indicating to the user of the first device any deviations between the second and fourth sequences, which is an indication of how intelligible the first sequence of information was after being transmitted to the second device.

The method for monitoring communication quality between at least two devices comprising receiving input from a user of the first device, converting the input into a first sequence of information, transmitting the first sequence of information to the second device, generating a second sequence of information based on the input by extracting from the input at least one piece of information corresponding to a past time instant, generating a third sequence of information by means of the second device, wherein the third sequence of information corresponds to the output of the second device based on the first sequence of information, generating a fourth sequence of information based on the third sequence of information by extracting from the third sequence at least one piece of information corresponding to a past time instant, wherein the at least one piece of information is preferably time-stamped, comparing the second and fourth sequences of information to detect any aberrations there between, wherein each piece of information of the second sequence of information is compared to a corresponding piece of information of the fourth sequence of information, and indicating for each piece of information of the first sequence of information an indication of the level of human intelligibility of the output performed of the second device based on that piece of information.

Yet another embodiment of the method for monitoring the quality of video conferences involves reliably conveying, separately from interruptible video data, transcribed text along with concurrent physiological data relating to the remote video conference participant. Digital video data that was captured during a time interval at a location of a remote party is received onto a local device. The digital video data depicts the remote party. A digital image of the digital video data is captured at a first time instant within the time interval. A value of a remote party feature of the remote party is determined using the digital video data. The value of the remote party feature is determined remotely at the location of the remote party. Examples of the remote party feature include the instantaneous heart rate of the remote party at the first time instant, the average heart rate of the remote party over the time interval, the heart rate variability of heart beats of the remote party during the time interval, the average breathing rate of the remote party over the time interval, and the average pupil dilation amount of the remote party over the time interval. The value of the remote party feature is received onto a local device.

Audio data is received onto the remote device. The audio data captures sounds spoken by the remote party. The remote device converts the audio data into words of text. In one implementation, the remote device is the smartphone of the remote party. The audio data that is converted into a particular word of text was captured starting at the first time instant. The particular word of text is received onto the local device. The particular word of text and an indication of the value of the remote party feature are displayed in association with one another on the graphical user interface of the local device. In one implementation, the remote party is a mental health patient, and the particular word of text and the indication of the value of the remote party feature are displayed on the local device to a health professional.

In an adaptation of the novel method, the audio data is stored without storing any personal identifiable information of the remote party together with or linked to the audio data and without storing the digital video data together with or linked to the audio data.

In another embodiment, digital video data captured during a time interval at a location of a remote party is received onto a remote device. The digital video data depicts the remote party. Audio data is also received onto the remote device. The audio data captures sounds spoken by the remote party during the time interval. The remote device converts the audio data into words of text. The remote device also captures prosodic information describing the sounds spoken by the remote party during the time interval. The words of text are received onto a local device. The prosodic information corresponding to the sounds spoken by the remote party during the time interval that were converted into the words of text is also received onto the local device. The words of text and the prosodic information is stored in association with one another.

In an additional embodiment, video data containing a set of digital images that were captured remotely at a location of a patient during a time interval are generated on a remote device. In one implementation, the patient is taking part in a mental health therapy session through a video conference. An intermediate image of the set of digital images is captured at a first time instant within the time interval. The set of digital images depicts the face of the patient. A heart rate value of the patient is determined using the set of digital images. The heart rate value is determined remotely at the location of the patient. For example, the heart rate value indicates the instantaneous heart rate of the patient at the first time instant, the average heart rate of the patient over the time interval, or the heart rate variability of the patient's heart beats during the time interval. In one example, the heart rate value is determined by using photoplethysmography (PPG) to calculate the average heart rate of the patient during the time interval.

The heart rate value is received onto a local device. In one implementation, the local device is a laptop or PC of a health professional. Audio data is generated on the remote device. The audio data captures sounds spoken by the patient. The remote device converts the audio data into words of text. The audio data that is converted into a particular word of text was captured starting at the first time instant. The particular word of text is received onto the local device. The particular word of text and an indication of the heart rate value are displayed in association with one another on the graphical user interface of the local device.

Other embodiments and advantages are described in the detailed description below. This summary does not purport to define the invention. The invention is defined by the claims.

BRIEF DESCRIPTION OF THE DRAWING

The accompanying drawings, where like numerals indicate like components, illustrate embodiments of the invention.

DETAILED DESCRIPTION

Figure 1:
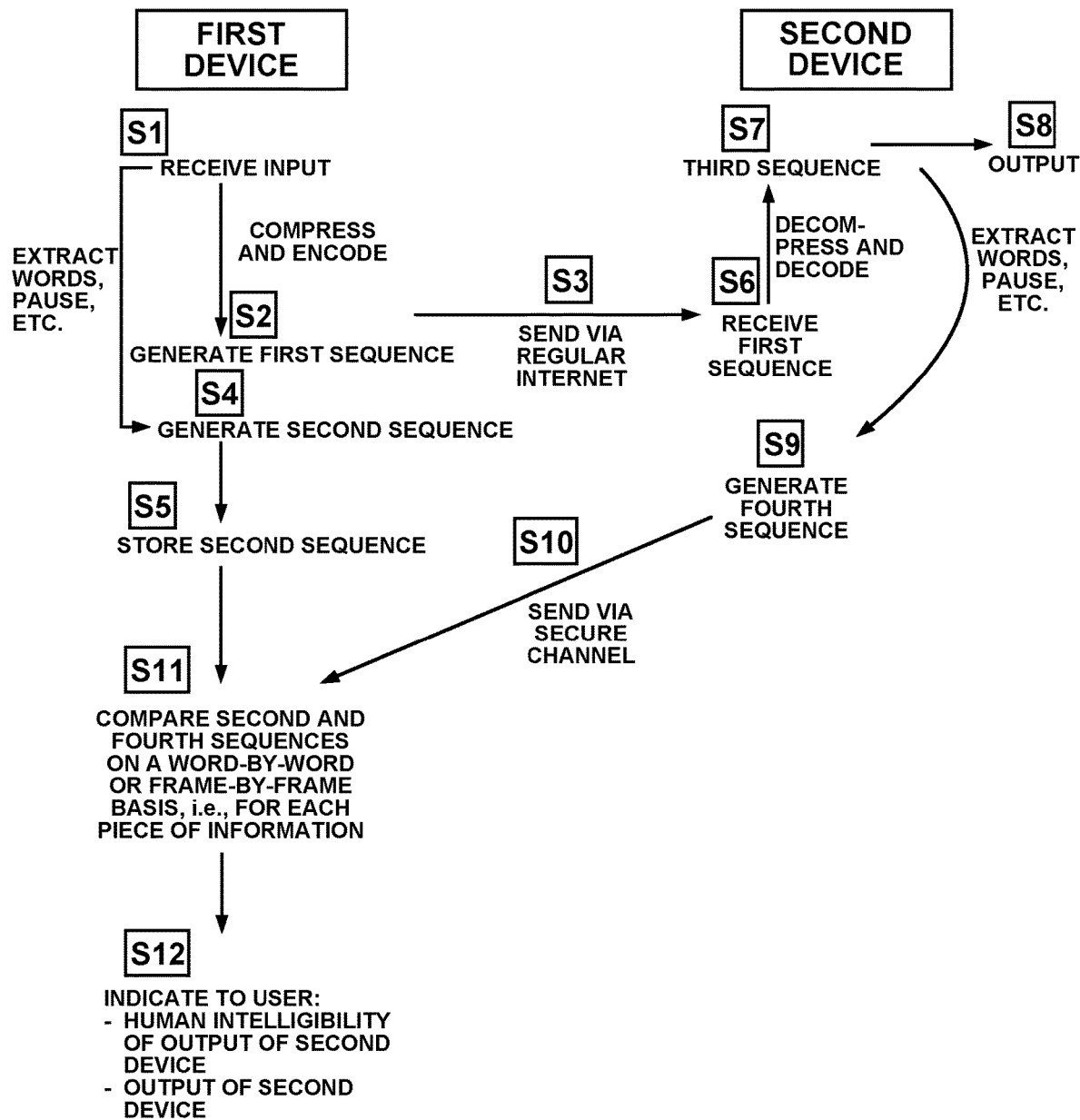
FIG. 1 shows a first embodiment of a method for monitoring call quality.

Reference will now be made in detail to some embodiments of the invention, examples of which are illustrated in the accompanying drawings.

A method is disclosed for monitoring the quality of communication between at least two devices, the method comprising:

receiving, by means of a first device, input from a user; converting the input received from the user into a first sequence of information; transmitting the first sequence of information to a second device; generating a second sequence of information based on the received input by extracting from the received input at least one piece of information corresponding to a past time instant, wherein the at least one piece of information is preferably time-stamped; storing the second sequence of information in the first device; generating a third sequence of information by means of the second device, wherein the third sequence of information corresponds to an output to be output by the second device on the basis of the first sequence of information;

generating a fourth sequence of information based on the third sequence of information by extracting from the third sequence of information at least one piece of information corresponding to a past time instant, wherein the at least one piece of information is preferably time-stamped; transmitting the fourth sequence of information to the first device; comparing the second and fourth sequences of information to detect any aberrations there between, wherein each piece of information of the second sequence of information is compared to a corresponding piece of information of the fourth sequence of information; and indicating, preferably displaying, by means of the first device for each piece of information of the first sequence of information an indication of the level of human intelligibility of an output performed by the second device based on this piece of information and/or preferably an indication of the output performed by the second device based on this piece of information.

The level of human intelligibility of an output performed by the second device may be indicated for example, by color-coded symbols, such as a bar moving with the progression of time that appears in red if human intelligibility at a given time instant is poor (e.g., due to a loss of words or audio signals being distorted, etc.) and in green if human intelligibility at a given time instant is good, e.g., no loss of information has been detected.

Preferably, a method according to the present invention focuses on the level of human intelligibility of transmitted information ("how well could a listening participant understand the content of the speech of a speaking participant during a videoconference") in contrast to focusing on the transmission fidelity at the level of bytes, data packages, or individual frames of a video ("how accurately was the speech transmitted"). For example, the loss of a single frame of a video stream or the loss of some audio data during compression or decompression may not impact the human intelligibility of the audio signal or message conveyed, e.g., another listening participant may still understand the speech of a talking participant of a videoconference. Such a loss of a single frame of a video stream or the loss of some audio data during compression or decompression may even be below the threshold of human perception and thus may not even be noticed by a listening participant of the videoconference.

In one embodiment, the method further includes the step: evaluating whether any detected aberration between the second and fourth sequences of information is above or below a threshold of human perception and/or is relevant to human understanding.

For example, it may be the case that only a single package of audio or video data was lost during transmission from the first device to the second device, but this data loss is negligible to a user of the second device because human beings do not understand audio or video output on a data-package or frame basis. For example, a user might not be able to notice that a single frame of a video was lost or that audio data relating to background noise was lost because the listening user still understands what the speaking user has said and also still understands the video transmitted. Thus, there may be data losses during transmission that one of the users of the devices or even both users cannot perceive and that are thus not relevant to human understanding of transmitted content. Preferably, the novel method of call quality monitoring is thus not focused on detecting any, including even minute, aberrations between a message or sequence of information sent from the first device to a message or sequence of information received by the second device, but is focused on detecting and preferably reporting aberrations that are relevant to human understanding of the message.

Current videoconferencing solutions do include flow control mechanisms, which allow them to cope with issues like variable communication delays or lost packets/packages of data. In these cases the goal is optimizing the call quality given the available communications channel. Nevertheless, all these flow control mechanisms do not go higher than the transport layer; this means that they focus on small pieces of information (packets or packages) but not on the whole human-understandable message. Based on this mechanism, it is feasible to analyze the link quality, for example by counting the amount of packets with errors, but it is not possible to analyze the human intelligibility of the received message. Furthermore, it is not possible identify whether packets are lost, as protocols such as User Datagram Protocol (UDP) do not provide mechanisms for that. In contrast to existing solutions, the novel method of call quality monitoring introduces new quality-analysis mechanisms at a high level to explicitly provide information to the user about the human intelligibility of the received message.

Aberrations that are expected above a threshold of human perception and/or are relevant to human understanding are identified and reported. For example, the message sent from the first device to the second device might be "I eat bread with oil," and the feedback message being sent back from the second device to the first device might be "I eat bread width oil." Thus, there appears to be an aberration in the speech signal recorded at the first device ("with") from the speech signal reproduced at the second device ("width") that is relevant for human understanding of the message (in contrast to, e.g., a packet of background noise being lost). In this case, the aberration may be indicated or reported to the user, preferably the user of the first device. However, judging how severe the aberration is and whether the aberration requires action from one of the users, for example by repeating the sentence, is left to the user. In the example of the first user of the first device saying "I eat bread with oil" and the message being reproduced by the second device of the second user as "I eat bread width oil," the user of the first device may judge that this aberration was not so severe for the other user to understand the message, and thus no repetition of the sentence is required.

In other words, this may offer the advantage that if aberrations between speech signals captured by the first device and audio signals reproduced by the second device are detected, these are only indicated to the user if they are relevant to human understanding of the speech signals. For example, during a video conference, background noise accompanying captured speech signals may not be accurately transmitted. This omission, however, does not compromise the human understanding of another participant of the video conference of the speech signals, so this aberration from absolute transmission fidelity may be regarded as irrelevant to assessing call quality. Similarly, there may be data losses during transmission that are not perceptible to a human participant in a video conference. Such aberrations from absolute transmission fidelity may also be regarded as irrelevant to assessing call quality.

At least one piece of information is extracted from the received input such that the at least one piece of information corresponds to an entity, such as a word, a number, a pause, a frame, an image, or a sound included in the input that is relevant for human intelligibility of the input.

For example, an entity such as a word or a pause that is relevant for human understanding of speech may be extracted from a continuous stream of audio data stemming from speech captured by the first device.

In one embodiment, the input received from the user is acoustic/audio input, preferably input relating to speech, and the input is converted into the first sequence of information by compressing and/or encoding. For example, the acoustic/audio input is first digitized by a microphone, and the digitized audio data is then compressed and/or encoded. Conversely, on the receiving side, the received compressed and/or encoded audio data is preferably digitized audio data that is converted into an analogue signal output by a speaker.

The second and fourth sequences of information are generated by a speech-to-text converter and include text. The second and fourth sequences of information may be regarded as summary messages of the human intelligible content of acoustic or audio signals captured by the first device and reproduced by the second device. The second and fourth sequences of information may each take the form of a file or a continuous stream and may be in text format. Similarly, the sixth and eighth sequences of information may each take the form of a file or a continuous stream and may be in text format.

In one embodiment, a separate communication channel and preferably a communication protocol configured to preserve information integrity to a high degree is used to transmit the fourth sequence of information between the first and second devices. In other words, the summary message of the human intelligible content of acoustic or audio signals captured by the first device may be transmitted in a separate channel from the channel used for transmitting the actual preferably encoded and compressed acoustic or audio signals from the first device to the second device. For example, the separate communication channel for transmitting the fourth and/or sixth sequences of information may use a transmission control protocol (TCP) communication protocol. The first and fifth sequences of information may be sent via a communication channel using a user datagram protocol (UDP) communication protocol.

According to an embodiment, the output performed or reproduced by the second device based on the third sequence of information is indicated to a user of the first device, preferably by displaying subtitles corresponding to acoustic signals, preferably relating to speech, output by the second device, on an output unit, preferably a screen, of the first device.

For example, the user of the first device may receive feedback in the form of subtitles of the content reproduced to the user of the second device ("what is received" or "what the user hears") based on the speech signals captured by the first device ("what is sent" or "what the user actually said"). Additionally or alternatively, the user of the first device may also receive feedback in the form of subtitles of the content sent to the user of the second device based on the speech signals captured by the first device ("what the first device captures from the actual speech of the user").

The indication of the level of human intelligibility of an output performed by the second device based on this piece of information of the first sequence of information can relate to a symbol, a font or a color code. For example, words that were omitted may be displayed in red, italics or strikethough or be indicated in brackets or with an asterisk. Words that were transmitted with a satisfactory degree of human intelligibility may be indicated in green or in a specific font, etc. Words that were added may be displayed, e.g., in blue, underlined or shown in square brackets, etc. Of course, not only the addition or omission of words can impact human intelligibility of the output, but also the speed at which, e.g., a word is reproduced or the delay with which the word is reproduced. Thus, the addition and omission or words, the scrambling of words, distortions in sounds, the reproduction speed of words etc. are all merely examples of factors that impact human intelligibility of the output performed by the second device. The novel method of call quality monitoring is thus in no way limited to these examples, but is applicable to any factor likely to impact human intelligibility of the output performed by the second device.

In an embodiment, the indication of the level of human intelligibility of an output performed by the second device based on this piece of information of the first sequence is directed to a different sensory modality of the user than the input received from the user. For example, if acoustic or audio data, such as speech signals, are captured from the user of the first device, the indication of the level of human intelligibility may be visual, e.g., by displaying subtitles.

In another embodiment, the second sequence of information may be generated directly out of the audio data acquired by the microphone without an intermediate step of processing the audio data, for example, by compressing and/or encoding. Of course, the second sequence of information may also be generated out of the audio data acquired by the microphone after the audio data has been processed, e.g., by encoding and compressing.

In another embodiment, the first device captures speech and provides digital audio. This digital audio is compressed and encoded and sent to the second device. The very same compressed and encoded digital audio signal is also uncompressed and decoded at the source side, thus generating a new digital audio signal. This new digital audio signal is then converted to text and stored (thus forming the second sequence of information) and compared later on, e.g., with the fourth sequence of information.

Although so far mainly the transmission of audio data has been discussed to illustrate the invention, the invention is not limited to audio data and is equally applicable to other data such as video data. It should be apparent for the person skilled in the art that if in an example, audio data has been described that is captured by a microphone and reproduced by a speaker, if the novel method is to be applied to video data, the video data is captured by a camera and reproduced by a display. Thus, in the example in FIG. 3, the first and second devices both include a microphone, a camera, a speaker and a display and thus can be used for applying the invention to both audio and video data although the example of audio data is described in more detail.

An identifier is added to each piece of information of the first sequence of information (that in this example corresponds to a stream of frames of a video acquired by a camera, e.g., of the first device). For example, consecutive numbers may be added to consecutive frames of the video. A second sequence of information is generated from the first sequence of information, wherein each of the pieces of information of the second sequence of information is linked to an identifier. For example, a pattern A extracted from the first frame is linked to the number 1 and a pattern B extracted from the second frame is linked to the number 2 of the second frame. At the level of the second device, a video is displayed based on the first sequence of information. From the displayed video, a fourth sequence of information is generated, wherein each of the pieces of information of the fourth sequence of information is also linked to an identifier. For example, a pattern A extracted from the first frame is linked to the number 1, and a pattern C extracted from second frame is linked to the number 2. If the sequences are compared on a frame-by-frame basis, it is apparent in this example that the first frame was transmitted correctly, because the first frame captured by the first device contained pattern A, and the first frame displayed by the second device also contained pattern A. Pattern A can be, e.g., a face. The second frame captured by the first device contained pattern B (e.g., a close-up of the face) and the second frame displayed by the second device contained pattern C (e.g., a hand). Thus, there is an aberration between the video recorded at the first device and the video displayed/reproduced by the second device. In other words, at the first device a pattern detector is run on each frame, and a list of extracted patterns is obtained. The same operation is performed by the second device for each of the received frames, and then the patterns extracted in both sides must coincide if the transmission was without any data loss.

In another embodiment, an identifier is added to each piece of information of the second sequence of information (e.g., a number is added to each frame extracted from a video stream). Thus, the second sequence of information may be regarded as a reference message of the video captured at the first device and may for example contain the sequence: frame 1, frame 2, frame 3, frame 4 indicating that four frames with identifiers in the form of consecutive numbers were contained in the video message sent from the first device to the second device. At the second device, the corresponding identifier is extracted from each piece of information of the fourth sequence of information. Thus, the fourth sequence of information may be regarded as a summary message of the video received by the second device and may contain the sequence: frame 1, frame 2, frame 4 indicating that only three frames (frames 1, 2 and 4) were contained in the video message reproduced by the second device. In other words, the identifiers of the pieces of the second and fourth sequences of information are compared to detect any aberrations of the first and second sequences of information corresponding in this example to the content contained in the video captured at the first device and the video reproduced at the second device. In other words, the camera of the first device may be regarded as providing the first sequence of information (in this case, a sequence of frames). An identifier is added to each of the frames (e.g., a frame number), and the sequence of frames with each frame bearing an identifier is sent to the second device. Thus, in this example, the sequence of frames with the identifiers can be regarded as the second sequence.

In another embodiment, the first device may send a stream of video frames to the second device wherein each frame contains an identifier, and the identifier is a stream of consecutive numbers. The second device may be configured to perform a plausibility check on the incoming video stream, for example, by evaluating whether the number of the identifier of each consecutive frame increases by 1. If the plausibility check indicates an error in the transmission, for example, if a frame with the identifier 4 follows on the frame with the identifier 2, this aberration is indicated to the user of the first and/or second device.

If, via a conference, video is also transmitted, it is possible that packets of video data or even whole frames may be lost. This can cause interruptions in the video stream and mismatches or synchronization issues between the audio and video channels. Adding an identifier to each piece of information, e.g., each frame of a video, allows such losses to be detected.

In one embodiment, a specific pattern may be added as an identifier to each of the frames or images. For example, a small number at a corner of the image, or at the area overlapped by the self-video, or the frame may be extended and the identifier may be added outside the part of the frame that is shown to the user. This identifier can change from frame to frame or image to image, for example, like a loop counter of three digits. At the receiver side, the reconstructed image can be analyzed and the value of this number can be extracted, verifying that the counter is following the expected pattern (for instance, increment by 1 at each frame or image) to verify that no frames were lost. The information regarding lost frames or received frames on the side of the second device can be sent, preferably time-stamped, to the first device and any aberrations or losses of frames relevant to human understanding or above a threshold of human perception may be indicated. For example, to display a set of multiple consecutive lost frames, a marker such as an asterisk can be added next to the subtitles indicating concurrent audio signals to denote the video disruption. For easy evaluation, the marker may be color-coded according to the number of frames lost (severity of the disruption).

Another aspect of the novel method of call quality monitoring is implemented on a device comprising:
  at least one input unit, such as a microphone;
  at least one output unit, such as a speaker;
  at least one conversion unit configured to convert input received from a user via the input unit into a first sequence of information;
  at least one extraction unit configured to generate a second sequence of information from the received input by extracting from the received input at least one piece of information corresponding to a past time instant, wherein the at least one piece of information is preferably time-stamped;
  a memory for storing the second sequence of information;
  at least one communication unit configured to transmit the first sequence of information to a second device and receive from the second device a fourth sequence of information, wherein the fourth sequence of information corresponds to at least one piece of information corresponding to a past time instant, wherein the at least one piece of information is preferably time-stamped and extracted from a third sequence of information corresponding to an output to be output by the second device on the basis of the first sequence of information;
  at least one comparison unit configured to compare the second and fourth sequences of information to detect any aberrations there between, wherein each piece of information of the second sequence of information is compared to a corresponding piece of information of the fourth sequence of information; and
  at least one evaluation unit configured to indicate for each piece of information of the first sequence of information an indication of the level of human intelligibility of an output performed by the second device based on this piece of information and preferably to indicate the output performed by the second device based on this piece of information.

In one embodiment, the evaluation unit is further configured to evaluate whether any detected aberration between the second and fourth sequences of information is above or below a threshold of human perception.

Preferably, the communication unit comprises a separate communication channel that preferably uses a communication protocol that preserves information integrity to transmit the fourth sequence of information.

According to an embodiment, the device comprises a screen, a communication detection unit configured to detect whether the device is communicating with at least one other device, preferably in an audio and/or video call, and a control unit configured to control, if the communication detection unit has detected that the device is communicating with at least one other device, the device to display on the screen an indication of acoustic signals, preferably vocal signal, captured by the device via the input unit, wherein the indication preferably comprises subtitles and/or an indication of acoustic signals output by the at least one other device, wherein the indication preferably comprises subtitles and/or at least one statistical indicator of communication quality, such as an indication of a background noise, a signal-to-noise ratio, a connectivity strength, a transmission delay or a synchronization delay.

Another aspect of the invention relates to a system comprising at least two devices configured to perform the novel, preferably at least one device according to the novel method of call quality monitoring. The system includes a first device and a second device, which includes at least one input unit, such as a microphone; at least one output unit, such as a speaker; at least one conversion unit configured to convert input received from a user via the input unit into a fifth sequence of information; at least one extraction unit configured to generate a sixth sequence of information from the received input by extracting from the received input at least one piece of information corresponding to a past time instant, wherein the at least one piece of information is preferably time-stamped; and at least one communication unit configured to transmit the fifth and sixth sequences of information to the first device, wherein the first device comprises a conversion unit configured to generate a seventh sequence of information based on the fifth sequence of information received from the second device, wherein the seventh sequence of information corresponds to an output to be output by the first device on the basis of the fifth sequence of information, and the first device further comprises an extraction unit configured to generate an eighth sequence of information from the seventh sequence of information by extracting from the seventh sequence of information at least one piece of information corresponding to a past time instant, wherein the at least one piece of information is preferably time-stamped, and the at least one comparison unit of the first device is configured to compare the sixth and eighth sequences of information to detect any aberrations there between, wherein each piece of information of the sixth sequence of information is compared to a corresponding piece of information of the eighth sequence of information.

In the system, the first and/or the second device include a comparison unit and/or an evaluation unit.

Preferably, the at least one communication unit of the first device and the at least one communication unit of the second device are configured to provide a separate communication channel that preferably uses a communication protocol that preserves information integrity and transmits the fourth sequence of information and/or the sixth sequence of information between the first and second devices. For example, such a communication channel may use the TCP communication protocol. Other data may be transmitted in another channel using the UDP communications protocol.

Another aspect of the invention relates to a memory device containing machine-readable instructions that when read by a device enable the device to perform a novel method for monitoring communication quality. The method involves receiving raw audio data onto a first audio and text analyzer 27, wherein the raw audio data includes a first timestamp indicating a first time and receiving decoded audio data onto a remote audio and text analyzer 29, wherein the decoded audio data was generated by decoding encoded audio data, wherein the encoded audio data was generated by encoding the raw audio data, and wherein the decoded audio data includes the first timestamp indicating the first time. The raw audio data is converted into a first fragment of text by the first audio and text analyzer 27. The decoded audio data is converted into a second fragment of text by the remote audio and text analyzer 29. The second fragment of text is received by the first audio and text analyzer 27. The first fragment of text is compared to the second fragment of text. An indication is displayed on a graphical user interface as to whether the first fragment of text exactly matches the second fragment of text.

Another method for monitoring communication quality involves receiving decoded audio data onto a first audio and text analyzer 27, wherein the decoded audio data was generated by decoding encoded audio data, wherein the encoded audio data was generated by encoding raw audio data, and wherein the decoded audio data includes a first timestamp indicating a first time. The decoded audio data is converted into a first fragment of text. A second fragment of text is received from a remote audio and text analyzer 29, wherein the raw audio data was converted by the remote audio and text analyzer 29 into the second fragment of text, and wherein the second fragment of text also includes the first timestamp indicating the first time. The first fragment of text is compared to the second fragment of text. It is indicated on a graphical user interface whether the first fragment of text exactly matches the second fragment of text.

Yet another method for monitoring communication quality involves receiving video data onto a first image recognition system, wherein the video data includes a first timestamp indicating a first time, wherein the decoded video data is received onto a remote image recognition system. The decoded video data was generated by decoding encoded video data, and the encoded video data was generated by encoding the video data. The decoded video data received onto the remote image recognition system also includes the first timestamp indicating the first time. The method involves recognizing, by the first image recognition system, a first pattern in the video data and recognizing, by the remote image recognition system, a second pattern in the decoded video data. The recognized second pattern is received by the first image recognition system. The recognized first pattern is compared to the recognized second pattern. It is indicated on a graphical user interface whether the recognized first pattern exactly matches the recognized second pattern.

FIG. 1 illustrates the steps of a method in which a video conference user speaks into a first device, and a corresponding audio signal is received by a second device and reproduced to another user listening to the second device. The following description focuses on audio signals for ease of description, but the novel method of call quality monitoring is similarly applicable to video signals.

In step S1, by means of a first device such as a smartphone or tablet, an audio signal is received from a user. In step S2, the audio signal is compressed and encoded to generate the first sequence of information. The compressed and encoded audio signal is then sent in step S3 to a second device, such as a smartphone or tablet, via the internet.

Based on the audio signal received from the user, the first device also generates in step S4 a second sequence of information by extracting from the received input at least one piece of information, for example a word or a pause contained in the audio signal or speech signal received from the user. This at least one piece of information is associated with a past time instant. For example, the second sequence of information can contain the information that, 5 ms ago, the user uttered the word "You". In this case, the past time instant is "−5 ms". The at least one piece of information is time-stamped. For example, the word "You" may be linked to an absolute time value, such as the Universal Coordinated Time (UTC), to indicate when the user uttered this word. Alternatively, the word "You" may be linked to a relative time value, for example "30 sec after starting the videoconference".

The second sequence of information may be regarded as the extracted content of the audio signal received from the user of the first device. In other words, the second sequence of information may be regarded as a reference message indicating the content, preferably the content as is intelligible to a human being, of the audio signal received from the user of the first device. For example, the second sequence of information can be generated through speech-to-text conversion in order to capture the meaning of the speech of the user of the first device. In step S5, the second sequence of information is stored in the first device. The second sequence of information may thus be regarded as a sender-side reference message.

In step S6, at the second device corresponding to the receiver-side, such as a smartphone or tablet, the first sequence of information is received. In step S7, a third sequence of information is generated at the second device, for example by decompressing and decoding the audio signal of the first sequence of information. In step S8, the decompressed and decoded audio signal of the third sequence of information corresponds to an output that is output by the second device on the basis of the first sequence of information. In other words, the third sequence of information may be regarded as reflecting the actual output, e.g., speech output via speakers of the second device, to the user of the second device. Whereas the first sequence of information may be regarded as what is actually said by the user of the first device, the third sequence of information may be regarded as what is actually reproduced by the second device.

In step S9, based on the third sequence of information, the second device generates a fourth sequence of information by extracting from the third sequence of information to be output to the user at least one piece of information, such as a word or a pause contained in the audio signal or speech signal. This at least one piece of information preferably corresponds to a past time instant, wherein the at least one piece of information is preferably time-stamped. The fourth sequence of information is generated in the same way as the second sequence of information. The fourth sequence of information is generated through speech-to-text conversion to capture the meaning of the speech reproduced by the second device to the user of the second device. The fourth sequence of information may thus be regarded as a receiver-side reference message. The fourth sequence of information is the extracted content of the audio signal that is reproduced and presented to the user of second first device. In other words, the fourth sequence of information is a reference message indicating the content, preferably the content as is intelligible to a human being, of the audio signal received by the user of the second device.

The second and fourth sequences use the same reference framework for linking the at least one piece of information to a past time instant and/or for time stamping, so that the second and fourth sequences of information can be compared on a piece of information-by-piece of information basis for each past time instant.

The pieces of information of the second and fourth sequences of information are co-registered in time in order to allow, for each point in time, a comparison of the pieces of information of the second and fourth sequences for this point in time. The same point of time is used as a reference for linking the at least one piece of information of the second and fourth sequences to a past time instant and/or for time stamping. If absolute timestamps are used, both the second and fourth sequences may rely on UTC. As using the same reference framework can be important for any comparison, the same applies to the sixth and eighth sequences. The term "co-registered" means that the second and fourth sequences are referenced to the same reference.

In step S10, the fourth sequence of information is then transmitted from the second device to the first device.

The fourth sequence of information is transmitted from the second device to the first device via the internet in a separate channel that is separate from the channel used to transmit the first sequence of information. There is a separation of the communication channels between the first and second devices for transmitting audio signals, such as the compressed and encoded audio data of the first sequence of information, and for transmitting extracted content of the audio signals, such as the fourth sequence of information. The channel of communication for transmitting the fourth sequence of information is configured to offer a higher level of cyber security and/or transmission fidelity than the channel of communication for transmitting the first sequence of information.

Generally, the amount of data transmitted in the channel of communication for transmitting the extracted content is significantly lower than the amount of data transmitted in the channel of communication for transmitting the actual compressed and encoded audio signal. Thus, transmitting the extracted content, e.g., the fourth sequence of information, in addition to the actual audio signal, e.g., the first sequence of information, will require only a negligible increase in processing power.

For example, the first sequence of information may include pieces of information relating to speech signals such as words, but may also include background noise as well information regarding volume, pitch and speed of the audio signal. The fourth sequence of information may be a file in text format generated through speech-to-text conversion and comprising only the human intelligible content "You should not do it."

In step S11, after the fourth sequence of information has been transmitted to the first device, the first device compares the second and fourth sequences of information to detect any aberrations there between. The comparison is preferably performed on a piece of information-by-piece of information basis for each past time instant. Each piece of information of the second sequence of information is compared to a corresponding piece of information of the fourth sequence of information. Preferably, time-stamped pieces of information of the second and fourth sequences of information are co-registered in relation to time.

For example, the piece of information of the second sequence of information corresponding to the past time instant of −5 ms is the word "You" because the user uttered the word "You" at that time point. The piece of information of the fourth sequence of information corresponding to the past time instant of −5 ms is the word "You" because the audio output to be reproduced to the user of the second device for that time point is the word "You". In this case, for the past time instant and/or piece of information there are no aberrations between the audio signal captured by the first device from the user (sender) and the audio signal reproduced from second device to the other user (receiver).

The past time instances and/or the pieces of information included in the sequences of information relate to entities relevant to the human understanding of the information contained in data from which the sequence of information was generated. For example, a piece of information may relate to a word or a pause identified in a continuous stream of audio data captured from a speaking user. Similarly, the continuous stream of audio data captured from a speaking user may be separated into discrete time instants corresponding to a word or a pause or another entity relevant to human understanding of the audio data. Thus, the term "past time instant" may also be understood as "past time interval."

For example, from the continuous stream of audio data captured from a user saying "You should not do this", the pieces of information "You", "pause", "should", "pause", "not", "pause", "do", "pause", "this", "long pause" may be extracted. Each piece of information relates to an entity contained in the audio data that is relevant to and captures a human understanding of the audio data.

Each piece of information may be time-stamped so that each piece of information is allocated to a past time instant. For example, the word "You" is allocated to −5 ms, the entity "pause" is allocated to −3 ms, and the word "should" is allocated to −2 ms. Thus, when comparing two sequences of information of this format, it is possible to compare the sequences of information on an information-by-piece of information basis and/or a past time instant-by-past time instant basis.

In principle, it is also possible to compare the second and fourth sequences of information without the use of timestamps. For example, the second and fourth sequences of information may be aligned to detect any aberrations therebetween. A correlation algorithm may be used to align the pieces of information of the second and fourth sequences to detect aberrations there between. As the comparison between the sixth and eighth sequences is similar to or the same as the comparison between the second and fourth sequences of information, any explanation made in this disclosure relating to the comparison of the second and fourth sequences of information may equally be applied to the comparison of the sixth and eighth sequences of information.

In step S12, the first device then indicates to the user (sender) for each piece of information of the first sequence of information an indication of the level of human intelligibility of an output performed by the second device based on this piece of information. This indication can take the form of subtitles of the audio output being generated by the second device to the user (receiver) based on the audio input captured by the first device. The first device may be used to provide feedback to the user (sender) regarding what was received by the user (receiver) of the second device.

For example, the user of the first device said, "You should not do this," but during the videoconference the word "not" was lost. So the user of the second device actually received the message, "You should do this." The user of the first device may in this case receive the indication that the word "not" was lost during the transmission. On the first device the subtitle "You should not do this" is displayed to indicate to the user of the first device that the word "not" has been lost. Alternatively or additionally, an indication of the output performed by the second device based on this piece of information may be provided to the user of the first device, in this example a subtitle reading "You should do this".

Subtitles are only one option for providing an indication for each piece of information of the first sequence of information of the level of human intelligibility of an output performed by the second device based on this piece of information, and any other suitable indication is also within the scope of the novel method of call quality monitoring.

The severity of any aberrations and/or the level of human intelligibility of each piece of information may also be indicated to the user, e.g., by using a color code that displays words transmitted with satisfactory transmission fidelity in green and indicates a word transmitted in a form that is not intelligible to a human being or that has been omitted completely in red or strike-through.

Figure 2:
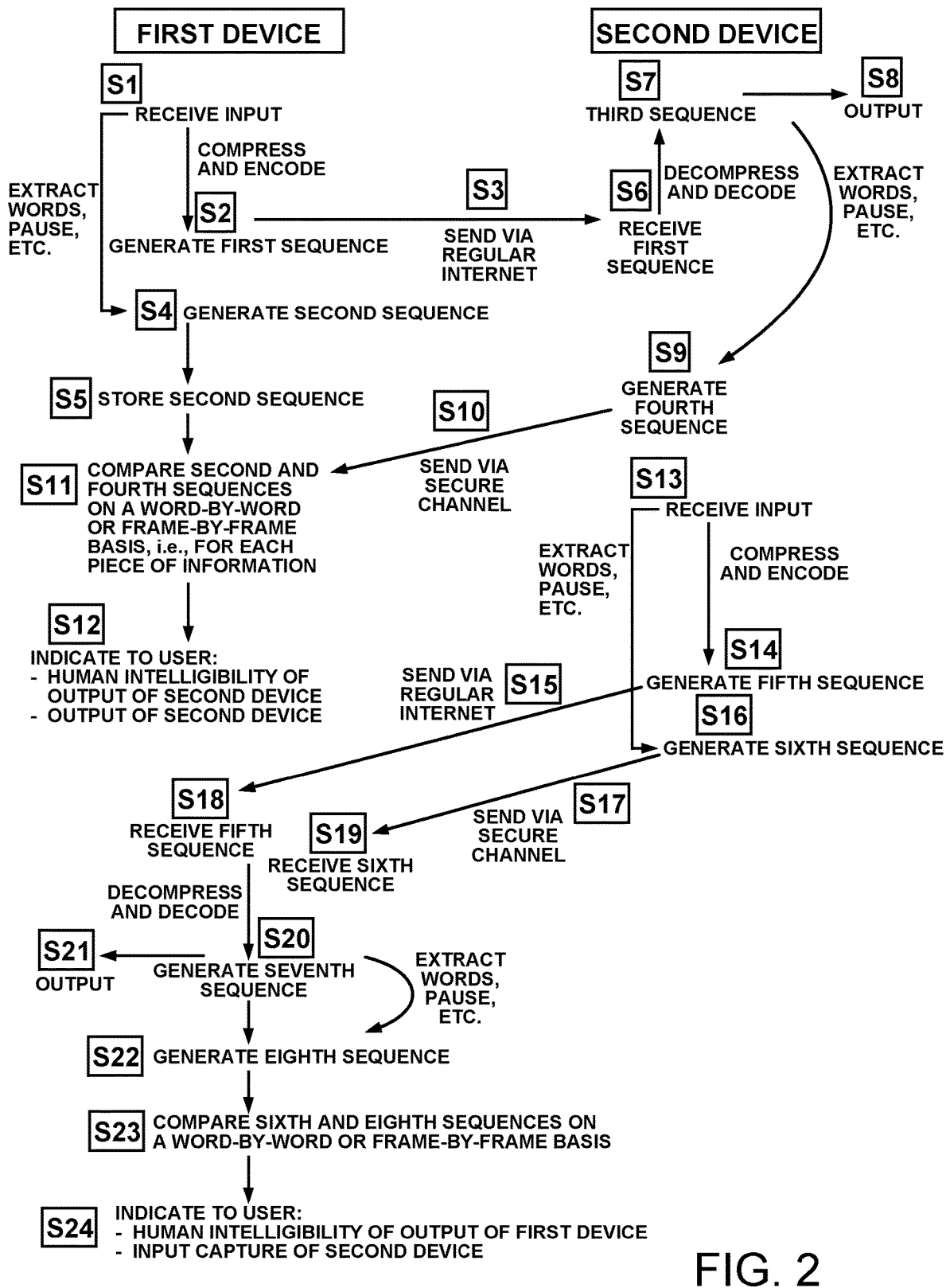
FIG. 2 shows a second embodiment of a method for monitoring call quality.

FIG. 2 shows another embodiment of the novel method of call quality monitoring. Steps S1-S12 of FIG. 2 correspond to steps S1-S12 of FIG. 1, and thus a redundant description of these steps is omitted.

In step S13, input from a user, e.g., an audio signal such as a speech signal, is received by the second device. This audio signal is then compressed and encoded to generate a fifth sequence of information in step S14. The compressed and encoded audio signal is then sent in step S15 to the first device, such as a smartphone or tablet, via the internet.

Based on the audio signal received from the user, in step S16 the second device also generates a sixth sequence of information by extracting from the received input at least one piece of information, such as a word or a pause contained in the audio signal or speech signal received from the user. This is the same or similar to the generating of the second sequence in step S4 by the first device.

In step S17, the sixth sequence of information is then transmitted via a separate secure communication channel to the first device.

In step S18 at the first device (corresponding to the receiver-side in this example), e.g., a smart-phone or tablet, the fifth sequence of information is received. In step S19, the sixth sequence of information is received.

In step S20, a seventh sequence of information is generated by means of the first device, for example, by decompressing and decoding the audio signal of the fifth sequence of information. In step S21, the decompressed and decoded audio signal of the third sequence of information corresponds to an output that is output by the second device on the basis of the first sequence of information.

In step S22, based on the seventh sequence of information, the first device generates an eighth sequence of information by extracting from the seventh sequence of information at least one piece of information, such as a word or a pause contained in the audio signal or speech signal to be output to the user.

Then in step S23, the first device compares the sixth and eighth sequences of information to detect any aberrations there between. The comparison is preferably performed on a piece of information-by-piece of information basis for each past time instant. The comparison is performed in the same or a similar way to the comparison described in step S11.

In this example, the first device in step S24 then indicates to the user (in this instance acting as the receiver) for each piece of information of the first sequence of information an indication of the level of human intelligibility of an output performed by the first device based on this piece of information, as well as an indication of the content of the audio signal captured by the second device, e.g., what the user of the second device said. The indication is performed in the same or a similar way to the indication described in step S12.

Figure 3:
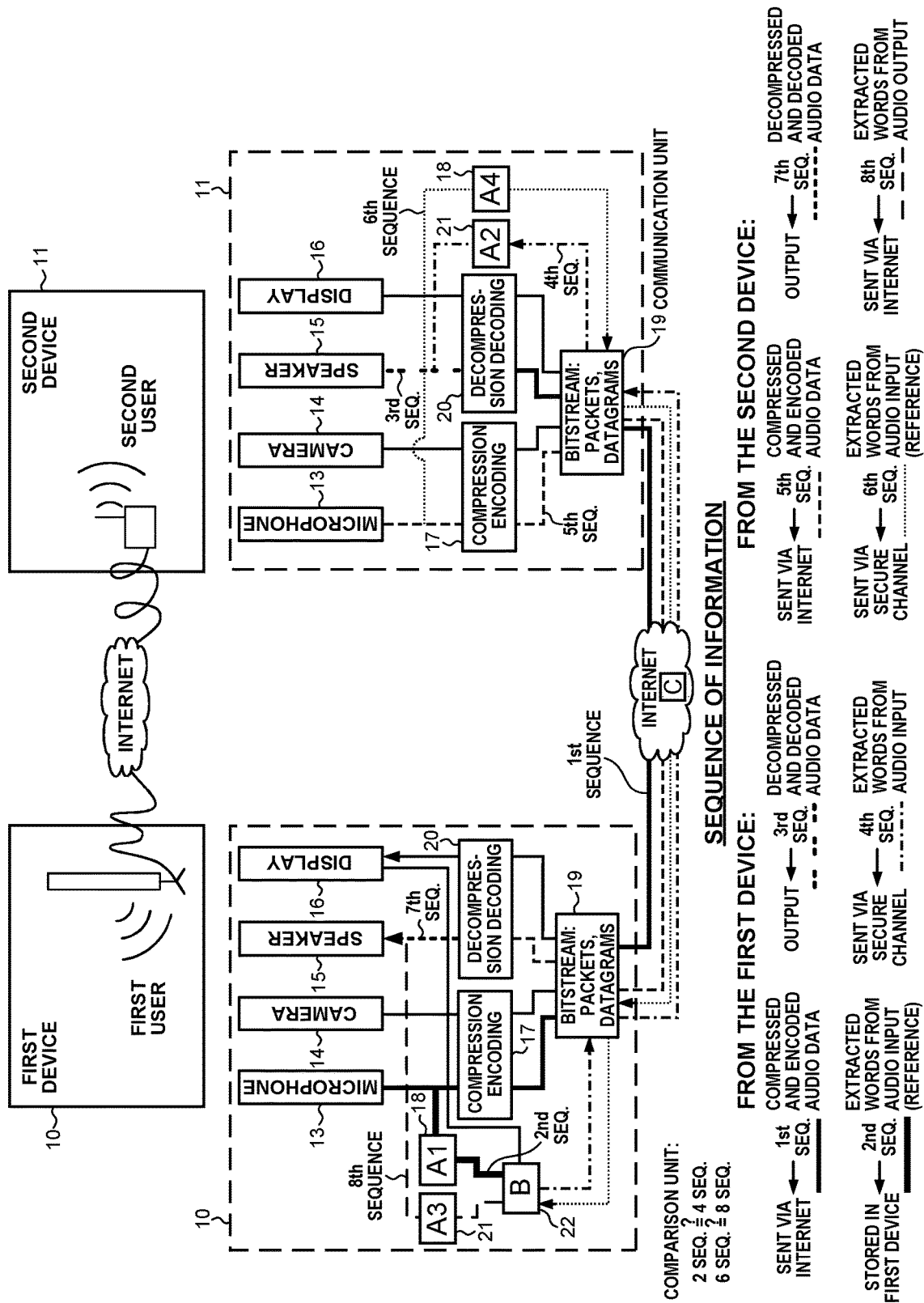
FIG. 3 shows a third embodiment of a method for monitoring call quality.

FIG. 3 shows a system for monitoring call quality that includes a first device 10 and a second device 11 that are used by a first and second user, respectively, to carry out a videoconference and preferably to perform the methods of FIGS. 1-2.

The first device 10 includes a microphone 13 and a camera 14 for receiving input from the first user and a speaker 15 and a display 16 for outputting or reproducing output to the first user. The first device 10 includes a conversion unit 17 configured to compress and encode audio signals, e.g., the input received from the first user. The first device 10 also includes an extraction unit 18 configured to extract entities relevant to human understanding from the received audio input, e.g., speech of the first user. The extraction unit 18 in this example is a speech-to-text converter that generates a text file from the captured speech. The first device 10 further includes a memory in which the text file is stored.

The first device 10 also includes a communication unit 19 configured to transmit data to the second device 11 and receive data from the second device 11. The communication unit 19 is configured to communicate with the second device 11 via two separate channels that exist simultaneously. In this example, one channel is used for sending the compressed and encoded audio signal received from the first user from the microphone 13, and the second channel is used to send the text file generated by the extraction unit 18.

The second device 11 receives the compressed and encoded audio signal via the communication unit 19 and decompresses and decodes the audio signal via a conversion unit 20 configured to decompress and decode audio signals.

Based on the decompressed and decoded audio signal, the second device 11 outputs an audio signal via the speaker 15.

From decompressed and decoded audio signals representing the audio signal sent to the speaker 15 of the second device 11, entities relevant to human understanding from the audio output are extracted using an extraction unit 21. The extraction unit 21 in this example is a speech-to-text converter that generates a text file from the audio signal indicating the acoustic output to be reproduced to the user. The text file generated by the extraction unit 21 of the second device 11 is sent via the communication unit 19 of the second device 11 to the communication unit 19 of the first device 10.

The first device 10 also includes a comparison unit (B) 22 configured to compare the text file generated by the extraction unit (A1) 18 of the first device 10 with the corresponding text file generated by the extraction unit (A4) 18 of the second device 11 received from the second device 11.

Referring to the methods of FIGS. 1-2, the comparison unit 22 of the first device 10 in FIG. 3 compares the second sequence of information to the fourth sequence of information and/or compares the sixth sequence of information to the eight sequence of information. In order to avoid redundant description, FIG. 3 indicates which line in the diagram corresponds to which sequence of information. In addition, the first device 10 includes an evaluation unit configured to evaluate the level of human intelligibility of the output generated by the second device 11 based on encoded and compressed audio data sent to the second device 11 by the first device 10 and to indicate the output generated by the second device 11 on the display 16 of the first device 10.

The system of two devices as shown in FIG. 3 is only one embodiment. A system that implements the novel method of call quality monitoring may also include at least two devices each configured like the first device 10 in FIG. 3 or at least two devices each configured like the second device 11 in FIG. 3. In other words, FIG. 3 may be described as follows: The underlying idea of this exemplary embodiment is to convert the speech captured by the microphone 13 at the first device 10 into text and store it. Then, at the second device 11, the audio signal that is to be reproduced at the speakers (which, in principle, should correspond to the speech recorded at the first device 10) is also converted into text, such as a string of text. This string is then sent to the first device 10, where it is compared to the stored text and then displayed on the screen 16. Note that this process involves analyzing the human-understandable message at the application level. This process also identifies past time instants and indicates quality (message intelligibility).

For example, the user of the first device 10 speaks a sentence. These words are captured by the microphone 13 and digitized; these digital audio samples preferably form a raw audio signal. The raw audio signal is encoded, compressed and transmitted to the second device 11. The raw audio signal is also delivered to software module A1, the extraction unit 18. Software module A1 performs speech-to-text conversion. The output of software module A1 is a string with timestamps, preferably a sequence of characters forming words that form sentences. Therefore software module A1 is configured to receive a continuous digital input stream corresponding to the analogue audio signal captured by the microphone. Sometimes some processing is performed on the input audio signal, such as to reduce background noise. Alternatively, the input signal provided at the input of software module A1 may be a processed signal coming from the videoconference system (e.g., a filtered signal). The input signal could also be the compressed signal, or the compressed, encoded and decoded signal (all done at the first device 10), which could be used to evaluate whether there is too much signal compression which compromises the intelligibility of the content. The software module A1 can also be configured to split the continuous input data stream into segments to process each of them simultaneously. This requires a memory to store segments of the incoming signal. Each of the segments is analyzed, possibly using a trained model or based on machine learning techniques, to translate the sequence of raw audio samples into words.

The incoming audio signal can be time-stamped based on a synchronization device such as an internal clock. The term "time-stamped" preferably means that each sample in the raw signal has a value that identifies the moment in time when it was acquired; for instance, the time elapsed since a reference event or a value in UTC format (e.g., Jan. 28th 2022, 17:03:01.23). The reference event can be an absolute time instant (e.g., 1st of January of 1970 at 00:00:00 UTC) or a relative time instant (e.g., the moment when the device was turned on). The timestamp may not be explicit for all timestamp samples; only a few values or parameters may be stored, and the rest can be calculated or inferred.

Because the novel method involves communicating through the internet, it is assumed that the internal clock is synchronized with an external reference such as the Network Time Protocol, NTP. Such synchronization typically can be performed with low error, in the range of milliseconds (i.e., small enough to be neglected in speech applications). After the speech-to-text conversion, the identified words can be time-stamped as well, indicating e.g., the moment when the pronunciation of the word started and the moment when the pronunciation of the word ended. Likewise the pause between words can be calculated as well. Alternatively, instead of relying on network time, even though it is very accurate, it is often simpler to rely on time periods elapsed from a well-defined starting point in time.

Figure 4:
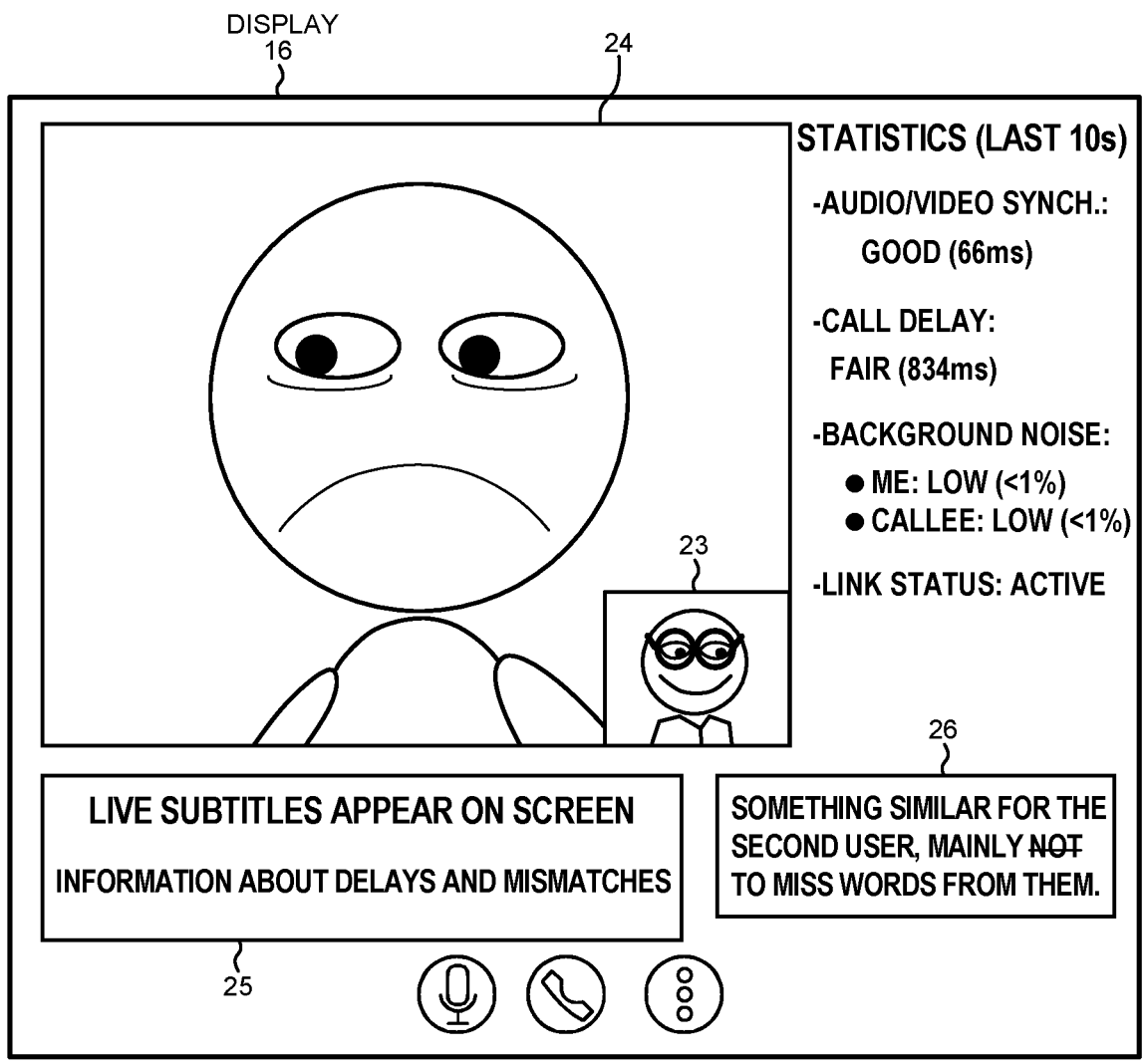
FIG. 4 shows an exemplary graphical user interface of a device used to implement a method for monitoring call quality.

The output of software module A1 (extraction unit 18) is delivered to software module B (comparison unit 22), which first displays the text on the screen 16 of the user of the first device 10, e.g., as shown in FIG. 4. The text displayed on screen 16 corresponds to the analysis or speech-to-text conversion carried out at the first device 10. For instance, the text may appear in white color. Besides the text itself, some information regarding the time length of the words, sentences or pauses may be displayed as well. While this is only an intermediate step, this information may already be valuable to the user of the first device 10.

Software module B causes the text to be displayed on the display 16 as soon as the text is available, in white color to indicate that this corresponds to the data directly captured by the microphone 13. Information about the time length can be displayed as well. This text corresponding to automatic subtitles of the speech of the first user can be used by the first user as an indication of whether the user is speaking clearly, too fast or too slow. For instance, if the speech-to-text system fails to identify the words, it may mean that the first user is not vocalizing clearly enough or that too much background noise is being captured by the microphone 13.

At this moment in time, software module B (comparison unit 22) waits for the information coming from the second device 11. If the first user keeps on talking, multiple text lines may be displayed at the first device 10 in the same way and with the same information as described above. If too many lines appear without feedback from the second device 11, this is already an indication that the communication is not working properly and an indication of an aberration may be displayed because the information coming back from the second device 11 is preferably automatic (no manual action).

In general, the novel method is fully automated for the user, as no explicit user input is required to send summary messages, such as the fourth and sixth sequences of information between the first and second devices.

In parallel with the process described so far, the digital audio signal that was delivered to software module A1 (extraction unit 18) is also encoded, compressed and transmitted via the internet to the second device 11. The second device 11 receives the data from the internet and reconstructs the message. This whole process from microphone capture at the transmitter through encoder, network transmission, receiver decoder, jitter buffer and finally playback naturally adds a delay. Ultimately an audio signal is reconstructed and, as soon as it is available, is played at the speaker 15 of the second device 11.

At the moment that the digital audio signal has been reconstructed and is ready to be converted back to analogue to be reproduced at the speaker 15, it is also sent to software module A2 (extraction unit 21) of the second device 11. This module performs essentially the same operation as does software module A1 by converting the speech (reconstructed digital audio samples in this case) into text and timestamping it. The output (e.g., a text string with timestamps) is then sent back via the internet to the first device 10 and may be regarded as a summary of the message received by the first device 10. A text string (with timestamps) is much smaller than digital audio or video signals. The amount of information that is sent back from second device 11 to first device 10 is thus almost negligible compared to the amount of information that is sent when transmitting actual audio or video data. Because of the smaller size, this information can be sent via a protocol that guarantees information integrity, such as TCP, so that if a packet is lost, it is retransmitted until its reception is acknowledged at the other side. This eliminates the possibility of the original message being properly delivered but not properly notifying the sender (the message is lost on the way back).

Preferably the timestamps are absolute. If the clock synchronization is not accurate enough, a relative timestamp may be used. In both cases, the time length of each word, sentence and pause can be evaluated with high precision. If absolute timestamps are available, then it is also possible to evaluate the communication delay between the data captured by the microphone at the first device 10 and the audio reproduced at the second device 11. If using RTCP protocol (RTP control protocol), which is normally used for both audio and video communication, this delay can be straightforwardly monitored.

Software module A2 analyzes the speech of the user of the first device 10. When receiving the message at the first device 10, it is delivered to software module B. The received message is compared to the message that had been stored. This comparison is very simple because both messages include text strings (messages) and numbers (timestamps). The timestamps are compared to determine whether the audio signal was reproduced at the same speed and whether the pauses between words were properly respected. Note that the information loss can also involve losing the pauses, and then the words would be pronounced together one right after the other. With absolute timestamps, the communication delay can also be determined.

Alternatively, when only relative timestamps are available, the total delay can be estimated from the moment when the message was sent until the text corresponding to that message returns. While this leads to an overestimation of the delay (compared to the actual delay, it involves an additional speech-to-text conversion and must travel back), it also defines an upper bound for the delay. If this upper bound is already small enough, then so is the actual delay.

After having received the information and having compared it, the only task that remains to be performed is to display the information in a simple way for the user of the first device 10. For the speech part, the simplest way is to display text, such as subtitles. To acknowledge the reception and highlight the mismatches, a different color can be used. For instance, green may indicate matching text and time lengths; yellow may indicate time lengths differing more than e.g., 5%; red may indicate that either a word was not reproduced at the other side (red with strikethrough) or that an unexpected word arrived (red).

No action is automatically taken based on the differences. The differences are simply reported to the user of the first device 10 as a means for the user to evaluate the necessity of repeating part of the speech, for example.

The information may be displayed in different ways. For instance, regarding the delays and time lengths of the words and pauses, lines or numbers can be used instead of colors. The length of the line may indicate the time length of the word or pause. Two different lines can be used, one for the first device 10 and one for the second device 11, to compare the lengths of both lines and determine whether they are similar.

In one embodiment, the software modules A1-A4 shown in FIG. 3 are all identical to extraction unit 18. In another embodiment, the software modules A2-A3, which extract information from signals that travel across the internet, are slightly modified and denoted as extraction unit 21. The software module B is the comparison unit 22.

FIG. 4 shows an exemplary graphical user interface (GUI) of the novel system for monitoring call quality. For example, the graphical user interface may be on the first device 10 or second device 11. A video of two users or participants in a video conference is displayed on the graphical user interface. For example, if the GUI is the display 16 of the first device 10, a small video panel 23 shows the user of the first device 10, the first user which could be a physician. If viewed by the first user, the panel 23 shows the "self-video", i.e., the video captured of the first user during the video conference. The large panel 24 shows the second user, which could be a patient to whom a mental health treatment is being administered.

A panel 25 indicates to the first user the acoustic output that the second user received based on the captured speech signals from the first user. In this example, during the video conference, live subtitles appear in panel 25 while the first user is talking to indicate what the second user has received based on the captured speech signals from the first user. The information contained in the subtitles in panel 25 is an indication of delays, mismatches or omitted words. For example, if the first user said, "You should not do this," and the second user heard "You should do this" because the word "not" was lost during transmission, a subtitle in panel 25 appears that reads "You should not do this".

Similarly, in panel 26, live subtitles appear while the second user is talking to indicate what the first user has received based on the captured speech signals from the second user. Panel 26 thus assists the first user in recognizing whether any words from the second user were missed or omitted.

For example, the second user may reply to the message "You should do this" received by the second user with "I do want to". In this case, in panel 26 the subtitle "I do want to"

appears. This allows the first user to distinguish the situation in which the second user says "I do want to" without any loss in transmission from the situation in which the second user says "I do not want to" with the word "not" being lost in transmission because in the latter case the subtitle in panel 26 would read "I do not want to". In addition, general call quality statistics, such as the level of background noise, the audio and video synchronization, and call delay, are indicated to the first user on the GUI. In the example shown in FIG. 4, the general call quality statistics are displayed next to the panel 24.

Relating to audio and video synchronization, it is important to remember that the audio signal and the video signal are independent signals that can fall out of synchronization, especially when the communication channel is unreliable and multiple packets of data may be lost at once. In an embodiment that monitors both audio and video signals, an extracted frame number for the video signal can be sent together with the time-stamped text from the second device 11 to the first device 10. The comparison unit 22 (software module B) then analyzes whether the extracted number associated with a certain text matches the number that was added to the same text at the first device 10. Mismatches in this check reveal desynchronization at the second device 11. Automatic corrective actions may be taken (e.g., sending to the second device 11 a message indicating to duplicate a few frames to restore the synchronization) or the aberration can simply be reported to the user of the first device 10.

The call delay can be precisely evaluated based on the extracted frame number or the text generated by the speech-to-text conversion, in combination with absolute timestamps. Each extracted frame number or text from audio data may be time-stamped in order to define a pair of characteristic events with its corresponding time instant of reproduction at the second device 11. If relating to audio data, the speech-to-text conversion can be used to identify characteristic instants in the speech, like the beginning of a word. The pair of characteristic events are sent via the secure channel to the comparison unit 22, where the counterpart audio segment (or reference audio signal) can be found. Any delay is then evaluated as the difference between timestamps.

When absolute timestamps are not available, an upper bound for the delay can be determined. Instead of comparing, for a certain text element, the timestamp at the first device 10 with a timestamp at the second device 11, the timestamp at the first device 10 is now compared to the time instant when this particular text element was received again by the first device 10 via the secure channel.

In case of a video conference with multiple participants, for each of the participants the GUI as shown in FIG. 4 is displayed. In other words, the video conference with multiple participants is represented as multiple simultaneous video conferences with two participants. Alternatively, multiple panels 26 may be presented in one GUI as shown in FIG. 4, reflecting the messages received from different participants of the video conference.

Figure 5:
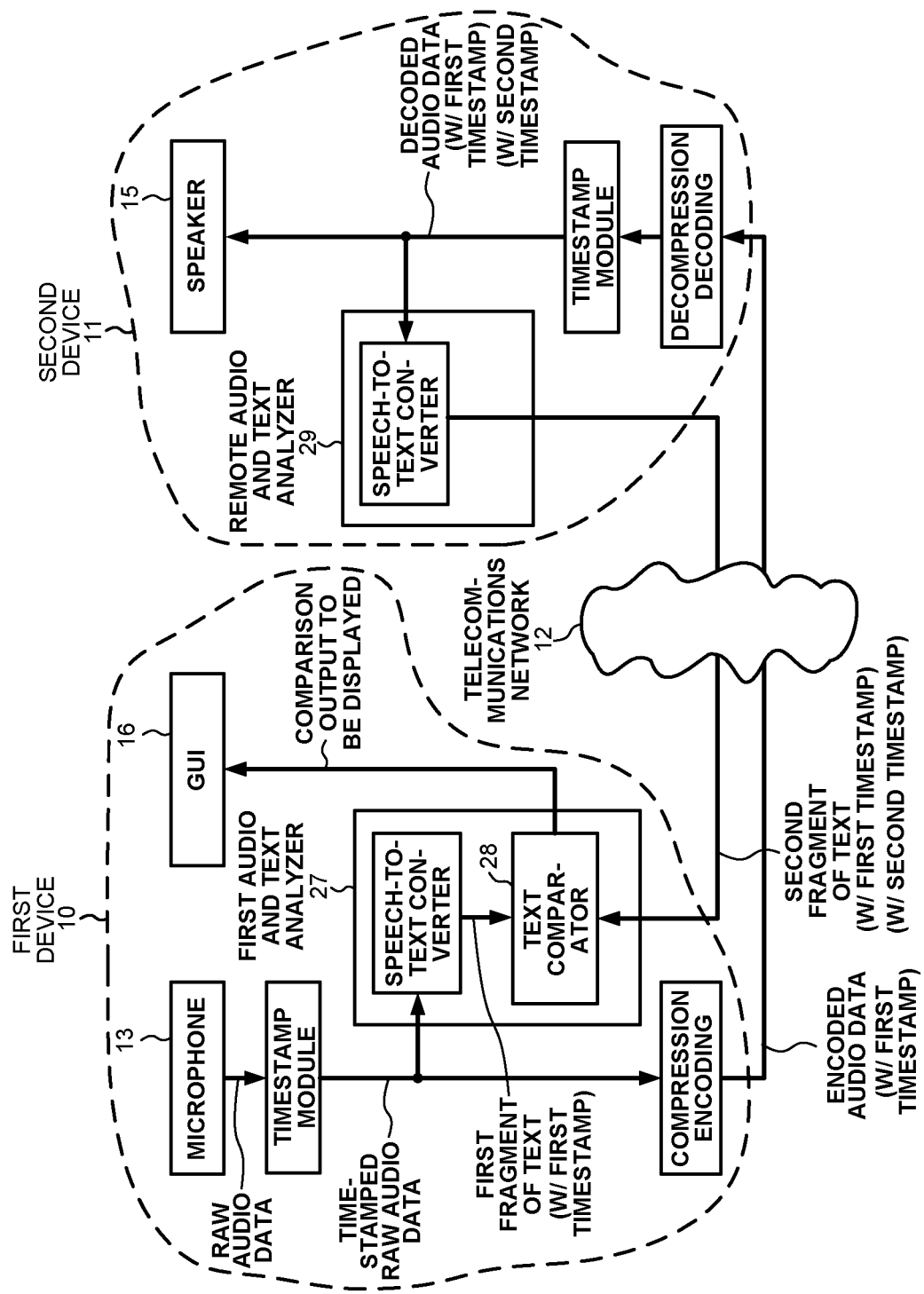
FIG. 5 shows a fourth embodiment of a method for monitoring call quality.
Figure 6:
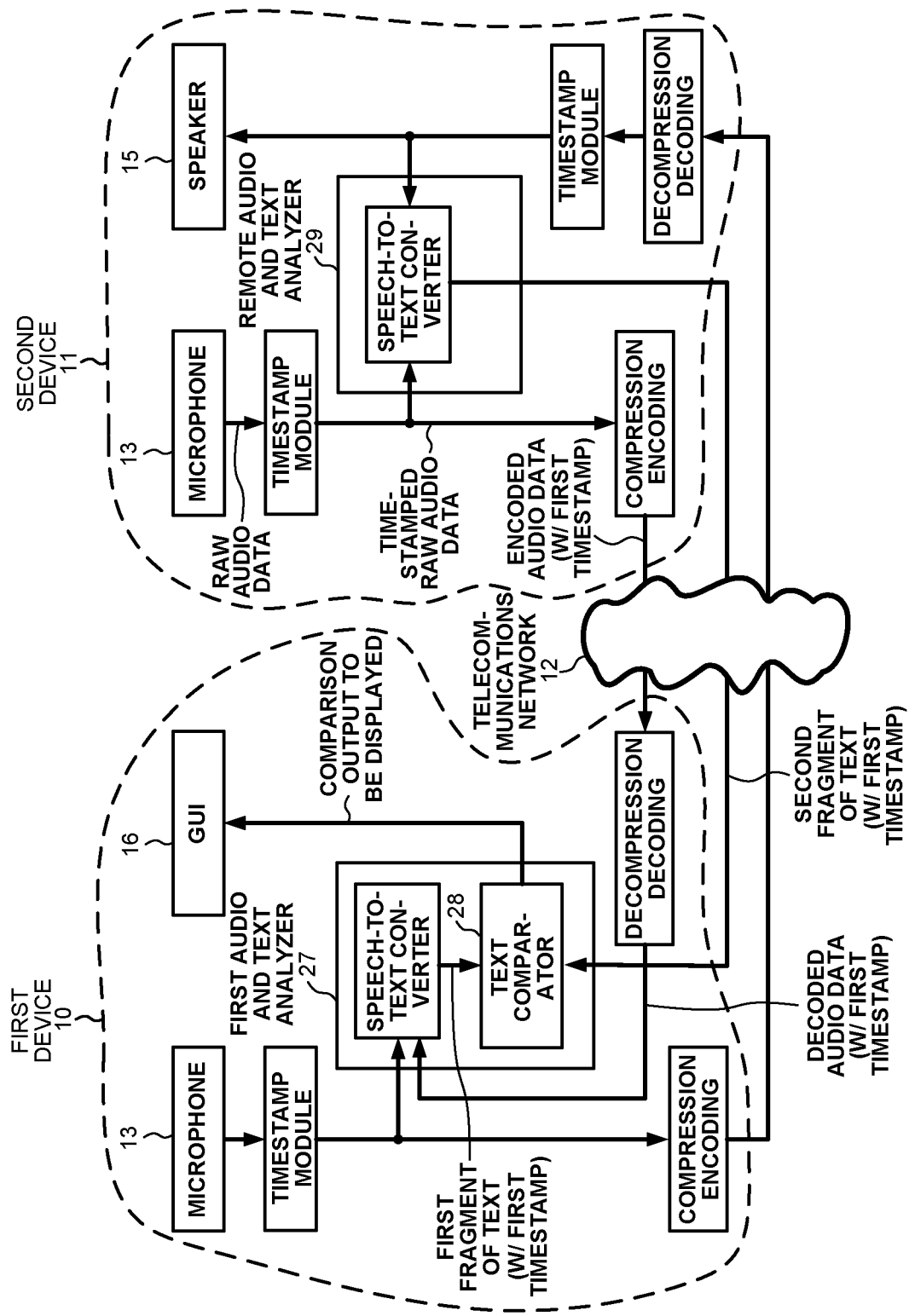
FIG. 6 shows a fifth embodiment of a method for monitoring call quality.
Figure 7:
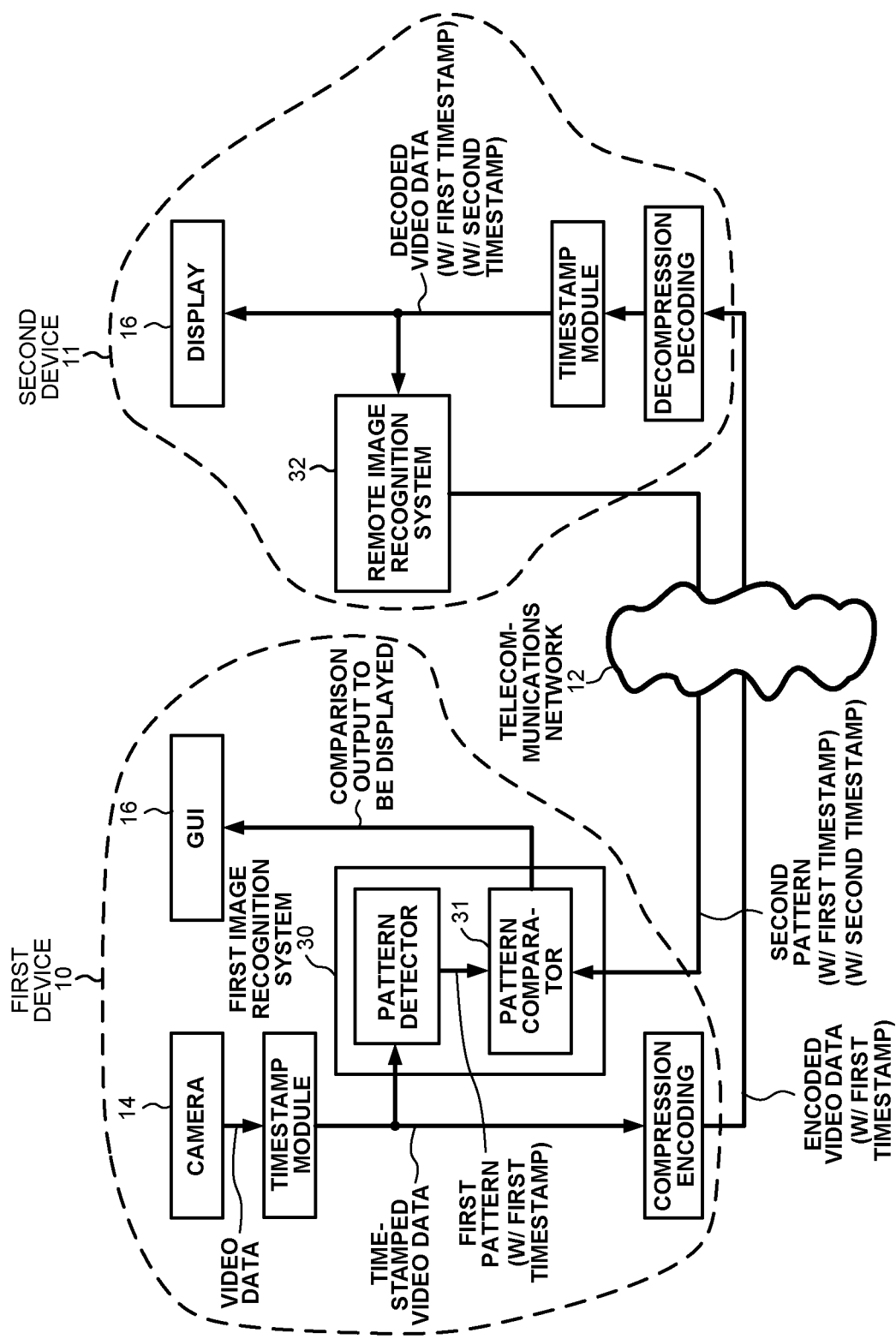
FIG. 7 shows a sixth embodiment of a method for monitoring call quality.

FIGS. 5-7 illustrate yet other embodiments of the novel system in which a first device 10 communicates with a second device 11 via a telecommunications network 12.

FIG. 5 illustrates a system that monitors the quality by which the speech of a user of the first device 10 is conveyed to a user of the second device 11. In one application, the user of the first device 10 is a physician or mental health profession who is remotely providing a mental health treatment to a patient who is the user of the second device 11. The physician can better deliver the mental health therapy if the physician is made aware of instances in which the physician's speech is not being accurately reproduced for the patient, such as due to poor transmission quality over the telecommunications network. Thus, the system of FIG. 5 is used to improve the delivery of telehealth and remote mental health therapies.

FIG. 5 illustrates that raw audio data representing the speech of the physician is acquired by a microphone 13 of a first device 10. The raw audio data is sent to a timestamp module to generate time-stamped raw audio data. The timestamp of the time-stamped raw audio data is just one of many timestamps that indicates, for example, the time instant at which the user began to speak a word. The time-stamped raw audio data is compressed and encoded to generate encoded audio data with a first timestamp.

The encoded audio data with the first timestamp is sent via the telecommunications network 12 to a second device 11. For example, the telecommunications network 12 uses the internet. At the second device 11, the encoded audio data is decompressed and decoded and input into a timestamp module to generate decoded audio data with a first timestamp and a second timestamp. Based on the decoded audio data with the first timestamp and the second timestamp, the second device 11 outputs an audio signal via speaker 15. The audio signal output by speaker 15 is the speech of the mental health professional that is presented to the patient, who is the user of the second device 11. The first timestamp indicates when the raw audio data was acquired (spoken by the physician), and the second timestamp indicates when the encoded audio data is received by the second device 11.

The time-stamped raw audio data is also input into a first audio and text analyzer 27 of the first device 10. The first audio and text analyzer 27 includes a speech-to-text converter and a text comparator 28. In the first audio and text analyzer 27, the time-stamped raw audio data is converted into a first fragment of text with a first timestamp by the speech-to-text converter. Then the first fragment of text with the first timestamp is input into the text comparator.

In the second device 11, the decoded audio data with the first timestamp and the second timestamp is input into a remote audio and text analyzer 29 of the second device 11. The remote audio and text analyzer 29 includes a speech-to-text converter that converts the decoded audio data with the first timestamp and the second timestamp into a second fragment of text with the first timestamp and the second timestamp. The second fragment of text with the first timestamp and the second timestamp is sent to the text comparator 28 of the first audio and text analyzer 27 of the first device 10. The text comparator 28 compares the first fragment of text with the first timestamp to the second fragment of text with the first timestamp and the second timestamp to determine whether the first and second fragments of text are exactly the same or the same to a degree that a human being would not detect any difference. The result of the comparison of the text comparator 28 is then displayed on the GUI of the display 16.

FIG. 6 shows the embodiment of FIG. 5 with some additional features used to indicate to the physician whether the speech of the patient has been accurately conveyed to the physician. In the system of FIG. 6, raw audio data in the form of the patient's speech is captured by the microphone 13 of the second device 11. The raw audio data is sent to a timestamp module to generate time-stamped raw audio data. The time-stamped raw audio data is compressed and encoded to generate encoded audio data with a first timestamp.

The encoded audio data with the first timestamp is transmitted via the telecommunications network 12 to the first device 10, where it is decompressed and decoded to generate decoded audio data with the first timestamp. The speech-to-text converter of the first audio and text analyzer 27 receives the decoded audio data representing the speech of the patient. The speech-to-text converter of the first audio and text analyzer 27 generates a first fragment of text with the first time stamp that is input into the text comparator 28.

At the second device 11, the time-stamped raw audio data representing the speech of the patient is also input into the speech-to-text converter of the remote audio and text analyzer 29, which generates a second fragment of text with the first timestamp. The second fragment of text with the first timestamp is transmitted to the first device 10 via the telecommunications network 12 and is input into the text comparator 28. The text comparator 28 then compares the first fragment of text, which was generated by speech-to-text conversion at the first device 10, to the second fragment of text, which was generated by speech-to-text conversion at the second device 11, the source of the speech by the patient. The result of the comparison of the text comparator 28 is then displayed to the physician on the GUI of the display 16 of the first device 10.

FIG. 7 shows an embodiment of the system for monitoring transmission quality where video data is being transmitted from the first device 10 to the second device 11. Video data is acquired by a video camera 14 of the first device 10. The video data is sent to a timestamp module to generate time-stamped video data. The time-stamped video data is compressed and encoded to generate encoded video data with a first timestamp.

The encoded video data with the first timestamp is transmitted via the telecommunications network 12 to the second device 11, where the video data is decompressed and decoded and input into a timestamp module to generate decoded video data with the first time-stamp and the second time stamp. Based on the decoded video data with the first timestamp and the second time stamp, the second device 11 displays an image and/or video on the display 16.

The time-stamped video data is also received by a first image recognition system 30 of the first device 10. The first image recognition system 30 includes a pattern detector and a pattern comparator 31. The pattern detector detects a pattern with the first timestamp in the time-stamped video data and sends the first pattern with the first timestamp to the pattern comparator 31.

The decoded video data with the first timestamp and the second timestamp is input into a remote image recognition system 32 of the second device 11. The remote image recognition system 32 includes a pattern detector. The pattern detector detects a second pattern with the first timestamp and the second timestamp in the decoded video data and sends the second pattern with the first timestamp and the second timestamp to the pattern comparator 31 in the first device 10. The pattern comparator 31 compares the first fragment of video data, which was generated by pattern recognition at the first device 10, to the second pattern of video data, which was generated by pattern recognition at the second device 11, which received the video data after it was transmitted across the telecommunications network. The result of the comparison of the pattern comparator 31 is then displayed on the GUI of the display 16 of the first device 10. The information shown to the user of the first device 10, such as a physician, indicates whether the video data displayed to the user of the second device 11, such as a patient, is an accurate reproduction of the video data generated by the camera 14 of the first device 10. For example, the comparison might indicate to the physician that some video frames were not transmitted to the patient but rather were missing from the video content displayed to the patient.

Figure 8:
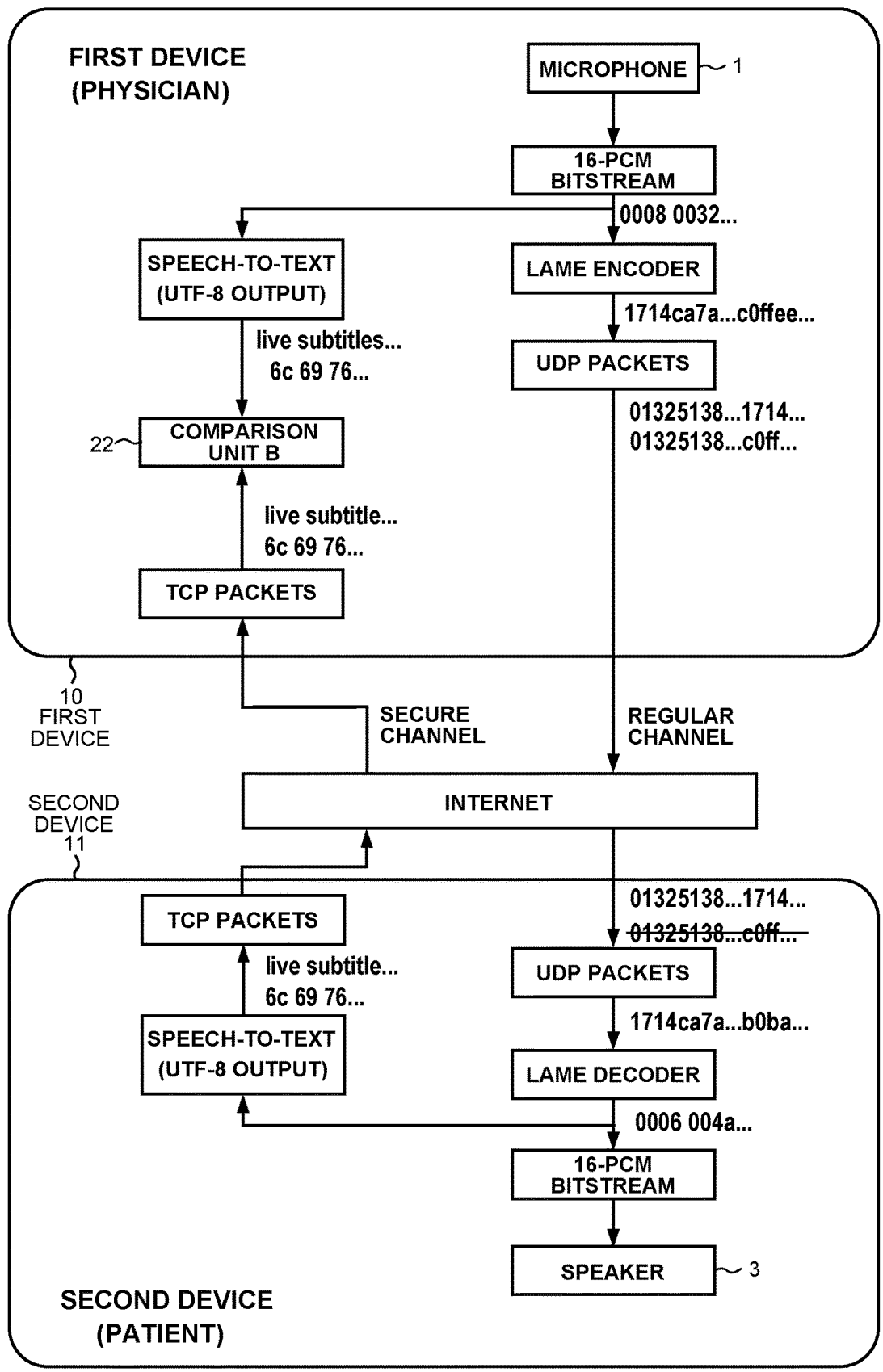
FIG. 8 shows a seventh embodiment of a method for monitoring call quality.

FIG. 8 is a diagram that provides more detail about how audio data is transmitted between the first device 10 and the second device 11 of the novel system. First, speech by the first user is captured by the microphone 13 of the first device 10. The acquired audio data, for example, takes the form of a pulse code modulation (PCM) bitstream showing the value of each 16-bit sample in hexadecimal. Two exemplary samples are displayed: 0008 and 0032.

The PCM bitstream is then converted, for example, by a LAME encoder that converts the input bitstream into another bitstream, for example into MP3-format. The encoded bitstream is split into segments. Two such segments are shown: 1714ca7a and c0ffee.

Each of the segments is sent in a user datagram protocol (UDP) packet to the second device 11. Two such packets are shown: 01325138 . . . 1714ca7a and 01325138 . . . c0ffee. The first numbers indicate the header, which does not contain audio data. After the header comes the body with audio data (the message). When transmitting the packages via the internet, some packets may be lost, as is indicated by the strikethrough in FIG. 8. In this example, the package 01325138 . . . c0ffee is lost during transmission.

The received UDP packets are unpacked by the second device 11, and a bitstream is created. Ideally, the unpacked content should be the same as the packaged content, but due to lost packets and errors, it may differ. The incoming bitstream is decoded by a LAME decoder, and an audio signal is recovered. Due to compression losses, even if no packages would have been lost, the exact original message may not be recovered.

In the first and second devices, the PCM bitstreams are sent to a speech-to-text conversion module, which converts the audio data or samples (e.g., a waveform) into a sequence of characters (in this example, encoded in UTF-8). For example, each group of 2 bytes corresponds to a character (6c->l, 69->i, 76->v, . . . ). The character "20" can be used to designate a split in the characters between words.

In contrast to the audio data that is being transmitted in UDP packets or packages, the output of the speech-to-text conversion module is sent as transmission control protocol packets or packages. Thus, there are two separate communication channels employing different communication protocols. A first channel using a UDP communication protocol and a separate second channel using a TCP communication protocol. The TCP protocol may be regarded as having a higher transmission fidelity and cyber security than the UDP communication protocol.

Simply comparing the words of the text fragments character-by-character or word-by word, or in a more general wording entity-by-entity, can reveal differences:

For example, the output of the speech-to-text conversion module of the first device 10 may be as follows:

6c 69 76 65 20 73 75 62 74 69 74 6c 65 73 20 61 70 70 65 61 72

And the output of the speech-to-text conversion module of the second device 11 may be as follows:

6c 69 76 65 20 73 75 62 74 69 74 6c 65 20 61 70 70 65 61 72

The output of the speech-to-text conversion module in this example is in 8-Bit UCS Transformation Format (UTF-8). The comparison unit 22 of the first device 10 compares these two output sequences. The output of the speech-to-text conversion module of the first device 10 includes an additional 73 between 65 and 20. This implies that the character corresponding to 73 was not received by the user of the second device 11.

Because of the timestamps, it is possible automatically to synchronize the output of the speech-to-text conversion module of the second device 11 with the output of the speech-to-text conversion module of the first device 10, without having to correlate signals.

The amount of data in bytes sent via the TCP channel is significantly lower than the amount of data sent via the UDP channel. For example, a person uttering the phrase "live subtitles appear on screen" leads to 2.8 s of audio signal corresponding to 22400 bytes of data to be packaged and transmitted. In contrast, the corresponding UTF-8 output of a speech-to-text conversion module converting the phrase "live subtitles appear on screen" into text corresponds to only 31 bytes. The amount of data required to transmit the same amount of human intelligible information is thus 1000 times smaller.

At the receiver side, the message "live subtitles appear on screen" may be reproduced as "life subtitles appear on screen". The difference in sound between the words "live" and "life", however, is small enough for the content/meaning of the message to be properly received.

In yet other embodiments of the novel method for monitoring the quality of video conferences, the system generates an enhanced video conference summary that includes information obtained from both the audio and video inputs. The summary incorporates additional data from the remote video conference participant, such as personal information and physiological data, alongside the transcribed text to contextualize the summary. The contextualized summary can be used for diagnosing the mental state of a remote patient in a mental health therapy session even when the video is interrupted or has low quality. The contextualized summary is thereby used to administer the mental health therapy. The contextualized summary can also be used to reduce the amount of stored data from a telehealth session when a contextualized summary of transcribed text is stored and is sufficient for later review, and the video file of the session can be deleted. The contextualized summary of transcribed text occupies much less memory space than does the video file.

The contextualized summary alleviates some of the disadvantages of performing telehealth sessions through video calls instead of in person. In conventional in-person mental health sessions, the health professional and the patient are usually sitting in the same room, facing each other and with a direct view of each other. The patient should be comfortably seated. During the session, various emotions are triggered in the patient, and those emotions may be externalized in various ways, such as through tone of voice, body language, facial expression or even crying. Some patients may not acknowledge such emotions or may even try to hide them. The objective of the health professional is not only to identify the patient's emotions, but also to determine what triggered those emotions. These tasks must be performed in order to diagnose and treat the patient. These tasks are complex, and thus health professionals rely on both verbal and non-verbal expressions from their patients. Not only is the patient's speech relevant, but also the context and manner in which the patient's responses are expressed and conveyed. It is therefore crucial for the health professional to be able to look at and listen to the patient during the entire time of the mental health session.

During a video therapy session, however, the video quality may randomly degrade. After a short interruption, the video session often resumes at a lower quality. The video quality may eventually recover after several seconds or a few minutes. Until that time, however, the video image may freeze, become pixilated or lose synchronicity with the audio. When this happens, it is no longer possible for the health professional to gather insights from non-verbal communication indicators, such as the patient's facial expression. Compared to in-person sessions, this is the equivalent of putting a sheet between the patient and the health professional, which substantially constrains the observed information that the health professional obtains during the in-person session. Consequently, when the video quality drops during a remote session, the health professional must either interrupt the session to restore the video quality (e.g., ask the patient to wait until the quality recovers or restart the video call) or carry on with the session and accept the information loss, which may ultimately compromise the therapy session. Likewise, if the image momentarily freezes, the health professional may not be able to distinguish a frozen image caused by communication interruption from a patient who remains very still reflecting on a question with the video working properly. This is especially critical for sessions with patients with catatonic depression, whose motor functions are impaired and they may move very slowly.

Sometimes the disruption in the communication channel is too large, and the video call drops. In general, after a few seconds, both participants are able to reconnect, and the video session can resume. Two problems can arise in this situation. First, the health professional may have been talking when the call dropped and then must either ask the patient to indicate the last words the patient heard before the interruption, or the health professional must repeat a larger portion of speech that the patient already heard. Second, the patient may have said something during the interruption (such as asking the health professional whether they are still connected) or may have moved or changed a physiological state (such as increased heart rate due to anxiety when the call dropped). During the interruption, the health professional misses these relevant insights that could have been used in the therapy session.

When the video quality of a mental health therapy session drops, it may no longer be possible for the health professional to gather insights from the video stream. The health professional may not be looking at the patient on the screen when the session drops, as the health professional might be taking notes. The novel contextualized summary of the video session is displayed as an on-screen summary of the recent call moments. Even if the video becomes unreliable or drops, the health professional receives the contextualized transcript and can proceed with the session. A summary of the last few sentences is displayed on the screen of the health professional with a scroll bar to browse through earlier call moments.

Health professionals often save the video data of remote therapy sessions for future reference. However, if the quality of the received video is low, it might not be possible to contextualize the speech in a future analysis from the low-quality video data. The novel method allows patient features to be extracted from the raw data at the remote location of the patient, which is unaffected by the quality of data transmission. The contextualized summary together with the patient features are transmitted to the health professional separately from the video data. When the health professional reviews the video file of a session at a later date, it is tedious and time consuming to locate the most relevant moments (e.g., to identify the highest patient arousal) manually by listening to the entire file. Moreover, this manual annotation is subjective because different professionals may provide different annotations to the same recording. The novel method identifies the moments in the therapy session at which the patient's measured physiological features passed defined thresholds.

The novel method of contextualizing a summary of a video conference can also be used to save storage space in computers and servers. Although remote therapy sessions can be saved as a video file to keep as much information as possible, this requires a very large amount of storage space. Storing only the transcribed text is not advisable because, while that requires only a fraction of the storage space, it involves losing a substantial amount of information, such as the tape locations of the patient's arousal. However, storing the transcribed text together with patient features allows the conversation to be contextualized with information related to the patient's mental state, while requiring only a fraction of the storage space compared to storing the entire video.

In the other embodiments, the contextualized summary is based on information from both the audio and the video signals. A number of patient features are extracted from the audio and video streams and can be used by the health professional during the therapy session. These features are extracted unobtrusively from the audio and video streams. The unobtrusiveness is advantageous because the measurement process does not influence the measured value from the patient. For example, heart rate is extracted via a photoplethysmogram (PPG), breathing rate is extracted from the patient's movement, pupil dilation is extracted from close-up images of the eyes, intonation and prosodic information is extracted from the audio data, and background noise is extracted from the audio data. In addition, combination features can be generated by combining multiple patient features, such as by combining the heart rate and background noise features. A combination feature can be generated by combining multiple features at the remote device. Alternatively, a combination feature be generated by combining multiple features at the local device that are received from the remote device.

The health professional uses prosodic information when interpreting the inputs provided by the patient during a remote therapy session. When reviewing the transcript of a therapy session, simply reading the words of the transcript may not be enough to properly diagnose a patient. Prosody describes characteristics of speech that concern phonetic units, such as syllables, words and sentences, and it describes aspects such as the rhythm, stress and intonation of speech. Prosody conveys meaning beyond the literal meaning, for example, by expressing viewpoint and attitude.

Prosodic information can be described in a phonetic file. The phonetic file can consist of a sequence of lines, each of them describing one sound or phoneme. An example of a phonetic file for the word "bonjour" is listed below:

; bonjour
_ 51 25 114
b 62
0 127 48 170
Z 110 53 116
u 211
R 150 50 91
_ 9

Each line begins with a character indicating the phoneme followed by a sequence of numbers. The first number expresses the length in milliseconds of the phoneme or sound. In the example above, the length of the sound "Z" (for the "j" in bonjour) is 110 milliseconds. The optional subsequent numbers that follow the first number define the pitch points of the sound. For example, the highest pitch point of the sound "Z" occurs at 53% of the 110-millisecond sound. The pitch at the highest pitch point has a frequency that is 16% higher than that of the starting pitch (at 100%). The underscore "_" indicates a silence. As the word "bonjour" was used in a sentence in the example above, there was a silence of 51 milliseconds between the beginning of the sound "b" and the end of the preceding sound. The prosodic information can be used to create a piecewise linear intonation curve of the input speech. In one embodiment, the contextualized summary of the video session includes prosodic information as well as other patient features.

In another embodiment of the contextualized video conference summary, transcribed text of a remote party's speech is reliably conveying, separately from the video data, along with concurrent physiological data of the remote party. In one particular application, the remote party is a patient who is taking part in a mental health therapy session with a health professional.

Figure 9:
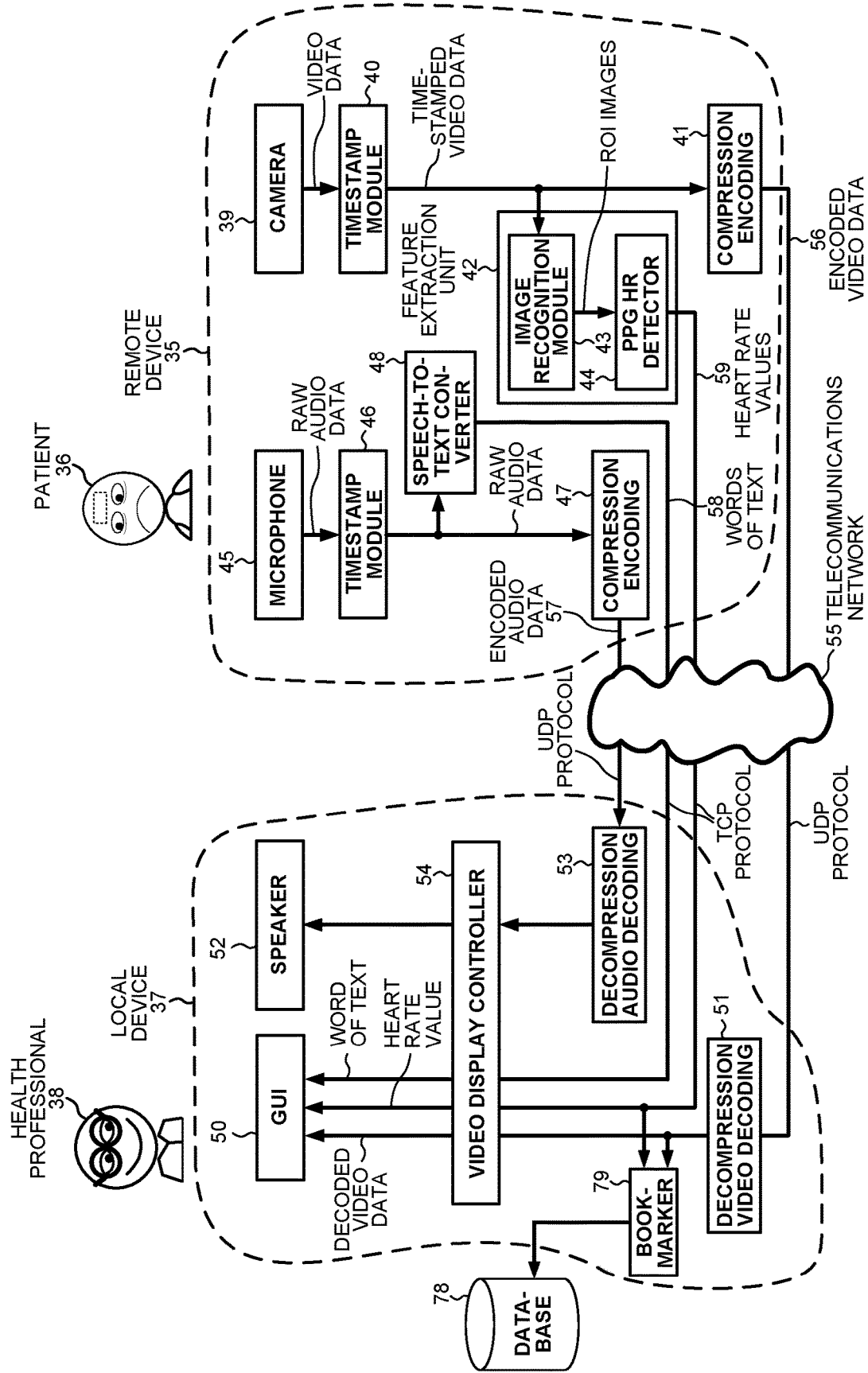
FIG. 9 is a schematic diagram of a video conferencing system that reliably conveys, separately from the video data, transcribed text along with concurrent physiological data relating to the remote video conference participant.

FIG. 9 shows a system that a health professional uses to administer a mental health therapy remotely to a patient. The remote patient takes part in a telehealth session using a video conferencing system that generates a contextualized summary of the video session. Transcribed text of the patient's speech along with an indication of the patient's concurrent heart rate is reliably conveying to the health professional separately from the video data, which is prone to periods of video signal interruption. The system for conveying the transcribed text of the patient's speech and concurrent physiological parameters of the remote patient includes a remote device 35 used by the patient 36 and a local device 37 used by the health professional 38.

Remote device 35 includes a video camera 39, an associated timestamp module 40, an associated compression encoding module 41, and a feature extraction unit 42. The feature extraction unit 42 includes a image recognition module 43 and a photoplethysmography (PPG) heart rate detector 44. Remote device 35 also includes a microphone 45, an associated timestamp module 46, an associated compression encoding module 47, and a speech-to-text converter 48. In one embodiment, remote device 35 is a smartphone and includes many more components than just those listed above, such as wireless communication modules. Moreover, the functionality of the components listed above can be implemented by mobile application programs, also known as mobile "apps". In one example, the image recognition module 43, the heart rate detector 44, and the speech-to-text converter 48 are implemented as software modules of a mobile app. In another example, the feature extraction unit 42 and the speech-to-text converter 48 are add-ons to commercially available video conferencing programs that typically run on personal computers and laptops. Alternatively, at least some of the functionality can be implemented as part of the operating system of the smartphone, such as an iOS mobile operating system or an Android mobile operating system. In other embodiments, remote device 35 is a tablet, a laptop or a personal computer.

Local device 37 includes a graphical user interface 50 (such as a screen, display or monitor) and an associated decompression and video decoding module 51, as well as a speaker 52 and an associated decompression and audio decoding module 53. Local device 37 also includes a video display controller 54 that synchronizes the various pieces of data received from remote device 35 based on the timestamps associated with the data. For example, video display controller 54 synchronizes the audio data and the corresponding video images. Video display controller 54 also displays on graphical user interface 50 words of text and the corresponding heart rate values that were generated from data that was timestamped at the same time instants. The system for remotely administering a mental health therapy also includes a telecommunications network 55 over which audio data, video data, the words of text and the heart rate values are transmitted between the remote device 35 and the local device 37.

In one embodiment, encoded and compressed video data 56 is transmitted with the user datagram protocol (UDP) communication protocol from the compression encoding module 41 on remote device 35 over the telecommunications network 55 to the decompression and video decoding module 51 on local device 37. In addition, encoded and compressed audio data 57 is transmitted with the UDP communication protocol from the compression encoding module 47 on remote device 35 over the telecommunications network 55 to the decompression and video decoding module 53 on local device 37. Words of text 58 that are generated by speech-to-text converter 48 are transmitted with the transmission control protocol (TCP) communication protocol from remote device 35 over the telecommunications network 55 to local device 37. The heart rate values 59 that are generated by feature extraction unit 42 are also transmitted with the TCP communication protocol from remote device 35 over the telecommunications network 55 to local device 37.

The TCP communication protocol preserves information integrity and ensures that data is reliably received by requiring the receiving device to return acknowledgements ("ACKs") confirming that each sequenced data packet has been received. Even though there is a delay from the TCP receipt confirmation and the buffering and post-processing of the heart rate calculation, the words of text 58 and heart rate values 59 usually do not arrive at local device 37 significantly later than does the corresponding video data 56 transmitted using the UDP communication protocol, which has no receipt confirmation, because the amount of data in the words of text 58 and heart rate values 59 is so much smaller than the amount of data in the video data 56. As soon as the words of text 58 and heart rate values 59 are received at local device 37, they are displayed on graphical user interface 50 regardless of which digital image of the video data is being displayed at that time.

Figure 10:
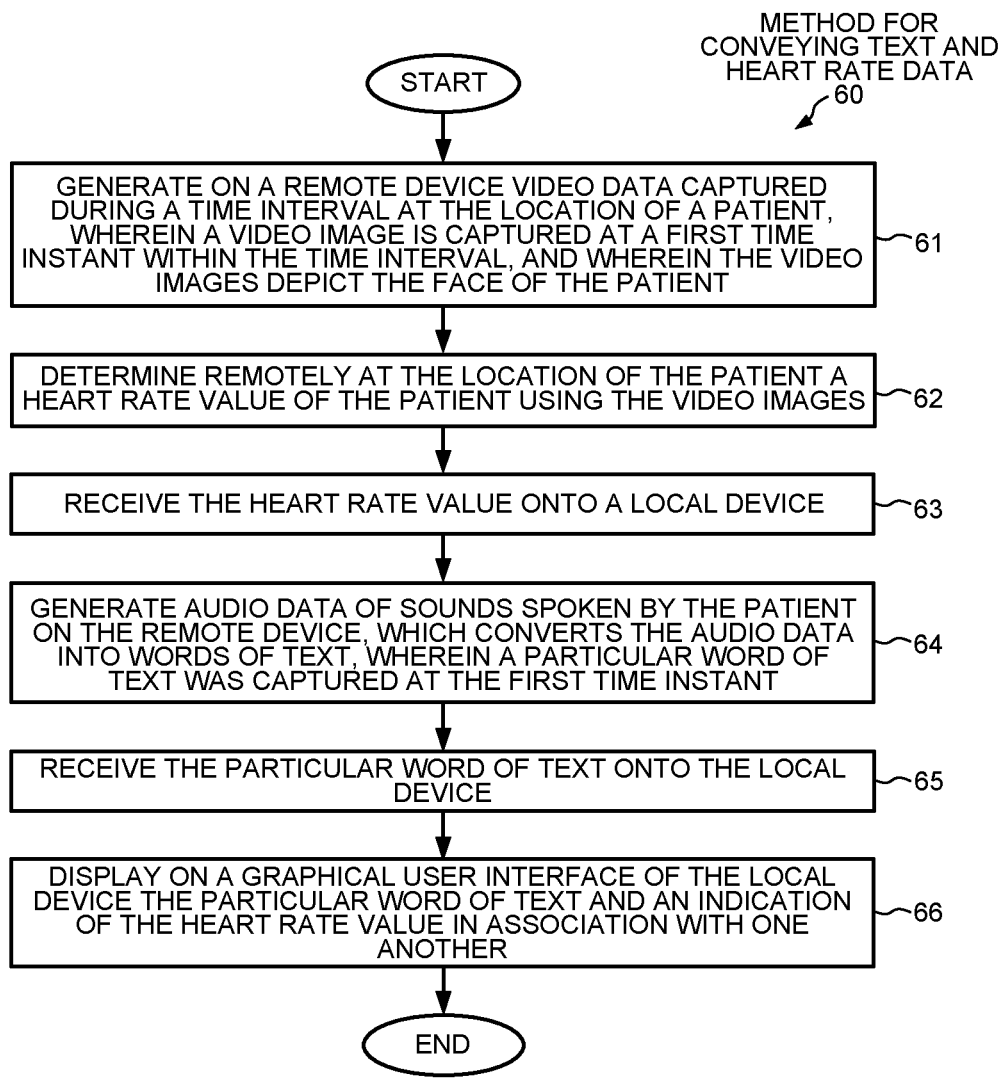
FIG. 10 is a flowchart of steps of a method for reliably conveying, separately from video data, transcribed text along with concurrent physiological data relating to a remote video conference participant.

FIG. 10 is a flowchart of steps 61-66 of a method 60 for conveying physiological parameters of remote patient 36 and concurrent transcribed text of the patient's speech from remote device 35 to local device 37 used by health professional 38. The steps of FIG. 10 are described in relation to the system of FIG. 9.

In a first step 61, video data containing a set of digital images captured during a time interval is generated on remote device 35 remotely at the location of patient 36. The video data is captured by video camera 39, which in this embodiment is the camera of the patient's smartphone. In one example, the video data is an uncompressed video stream of 1024×768-pixel, 8-bit color images transmitted at 30 fps, which corresponds to about 70 MB/s. The set of digital images depicts the face of patient 36. An intermediate image of the set of digital images is captured at a first time instant within the time interval. In a first implementation, the time interval is about three seconds, and an instantaneous heart beat is calculated in the time domain by determining the peak-to-peak length of a single heart beat. In a second implementation, the time interval is about ten seconds, and the average heart beat is calculated in the frequency domain by determining the average length of the heart beats during the time interval.

Figure 11:
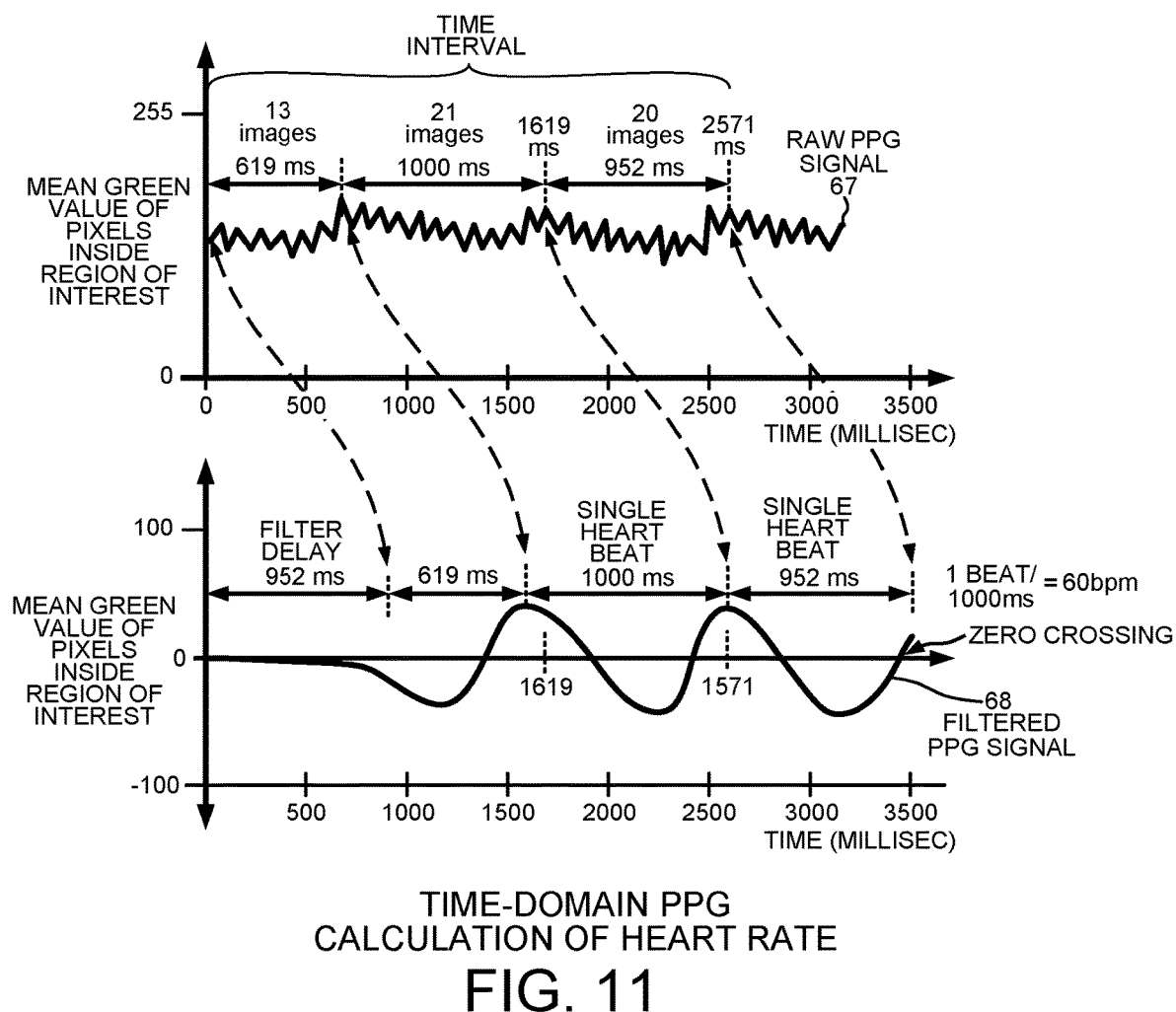
FIG. 11 shows a raw photoplethysmography (PPG) signal and a filtered PPG signal used to determine the instantaneous heart rate of a remote video conference participant.

FIG. 11 illustrates an example of the first implementation in which digital images are captured during a time interval of at least 2571 milliseconds. The intermediate image is captured at the first time instant, which occurs 1619 milliseconds after the beginning of the time interval. The novel method determines the instantaneous heart rate of patient 36 as of the first time instant. However, there is some delay in calculating the heart rate value, which is available to be transmitted to local device 37 about three seconds after the set of digital images begins to be captured and about 1.5 seconds after the first time instant. In this example, the digital images are captured every 47.62 milliseconds. Thus, there are 21 images captured every 1000 milliseconds, and a set of 54 digital images are captured during the time interval of 2571 milliseconds.

In second step 62, a heart rate value of patient 36 is determined using the set of digital images. In other embodiments, features other than heart rate are extracted from sensor data from the smartphone of the patient 36. Examples of such other features include: movement amplitude of the patient obtained from accelerometer data of the smartphone, background noise obtained by analyzing the audio stream from the smartphone's microphone, amount of ambient light determined from the video stream, speech mismatches between the health professional and audio data received by the patient by analyzing audio streams from the health professional's and patient's microphones, and prosodic information obtained by analyzing the audio stream from the patient's microphone. Complex features can be derived by combining various of the features listed above. Complex features can also be generated by directly using the data provided by multiple sensors on the patient's smartphone. The complex features can be generated by combining multiple features at the remote device. Alternatively, multiple features can be transmitted to the local device, where they are combined to generate a complex feature.

In step 62, the heart rate value is determined remotely at the location of patient 36. In the first implementation, the instantaneous heart rate value is determined using photoplethysmography (PPG) analysis on the digital images that are captured by video camera 39 and then timestamped by timestamp module 40 before being received by feature extraction unit 42. The time-stamped video data is also compressed and encoded by compression encoding module 41 to generate encoded video data 56 with timestamps, which is transmitted to local device 37.

In the feature extraction unit 42, the face of patient 36 is first recognized by image recognition module 43. Then a region of interest on the patient's face is defined that is used for the PPG calculations. In this example, the region of interest is a rectangular area on the forehead of patient 36, such as the dashed rectangle shown on the patient's forehead in FIG. 9. Typically, the video data consists of red, green and blue components of the color of each pixel in a digital image. In this example, the signal used for PPG calculations is made up of the mean green value of the pixels inside the region of interest of each digital image in the set of digital images. Thus, there is one PPG sample for each digital image. Consequently, in this example, one PPG sample is generated every 47.62 milliseconds.

The upper curve in FIG. 11 is the raw PPG signal 67, which is generated by the PPG heart rate detector 44. Each point on the raw PPG signal 67 is the mean green value of the pixels inside the region of interest of a particular digital image. The raw PPG signal 67 has a large "DC" component from the color of the patient's skin plus a smaller "AC" amplitude resulting from the variable amounts of green light absorbed by varying amounts of blood in the blood vessels close to the skin of the forehead. The green channel is used because hemoglobin in the blood absorbs green light more than red light. Hemoglobin appears red, which means that much of the color red is reflected as opposed to being absorbed. A larger mean green value signifies that less green light was absorbed, which corresponds to a smaller volume of blood flowing through the blood vessels. A smaller mean green value corresponds to a higher volume of blood flowing through the arteries immediately after the heart pumps. A camera with an 8-bit detector for each color captures the green values on a scale of 0-255. The typical "DC" component of the green value is between 80 and 230, and the typical "AC" component is less than 1. The amplitude of the "AC" component is typically smaller than the camera resolution because it is less than 1 bit. Therefore, the green values of all of the pixels in the region of interest are averaged in order to enhance the resolution. The amplitude of the "AC" component of the raw PPG signal 67 and of the filtered PPG signal 68 shown in FIG. 11 is greatly exaggerated for illustration purposes.

In the time-based approach of the first implementation, each new sample of the raw PPG signal 67 is filtered by a bandpass filter, which rejects the signal components that are outside the frequency range of a human heart beat, such as the low-frequency disturbances caused by breathing. The bandpass filter inherently introduces a delay because the inband content that is supplied at the filter's input appears at the output only after a number of samples, which depends on the filter. The computational delay, which is usually very small, is in addition to the delay caused by the filter itself. The lower curve in FIG. 11 is the filtered PPG signal 68. FIG. 11 illustrates that the "DC" component has been removed from the filtered PPG signal 68. FIG. 11 illustrates that the filter delay in this example is 952 milliseconds. This means that the peaks of the filtered PPG signal 68 correspond to peaks of the raw PPG signal 67 that occurred 952 ms earlier. A peak detector within PPG heart rate detector 44 then identifies the peaks of the filtered PPG signal 68. The peak detector also introduces an algorithmic delay of a number of samples because a peak can be identified only after it has occurred, and subsequent samples are determined to have lower values. Despite the filter delay and the peak detection delay, the heart rate value can be determined faster using the time-based approach of the first implementation than the frequency-based approach of the second implementation, which can determine the average heart rate for the 10-second time interval only after all of the samples in the time interval have been analyzed. For example, if the time interval used in the second implementation were to be shortened to the 3-second output time of the first implementation, then the accuracy of the average heart rate over the shortened time interval would be significantly reduced.

FIG. 11 illustrates that the filter delay is about 952 ms, which corresponds to a delay of about 20 samples. Then the peak detector in PPG heart rate detector 44 must wait until there is a zero crossing with positive slope to confirm that any subsequent negative slope signifies that a peak has passed. In the example of FIG. 11, this peak detection delay is 619 ms. The time between the first and second detected peaks is the length of time of a heart beat, in this example 1000 ms. An instantaneous heart rate value of one beat per 1000 ms corresponds to a heart rate of 60 beats per minute.

In another embodiment, the video data used to determine the heart rate is supplemented with PPG data from a wearable device, such as a ring or a wristband. Light is emitted from a light-emitting diode on the ring or wristband onto the finger or wrist of the patient, and a sensor measures the amount of light that was absorbed by the blood in the finger or wrist. This PPG data is transmitted using a short-distance protocol (such as Bluetooth) from the ring or wristband to the smartphone, where the heart rate detector 44 determines a second heart rate at the finger or wrist in addition to the heart rate at the forehead. This alternative remote party feature, which is based on two measured heart rates, indicates a change in the patient's blood pressure by comparing the heart beats at the patient's forehead with the heart beats at the patient's hand. Preferably, each heart rate value obtained from the video data and each heart rate value obtained from the wearable device are accompanied by timestamp values so that heart rates that were measured at the same time can be compared. Simultaneous timestamps on different devices, such as a smartphone and a wearable device, can be synchronized using network time protocol (NTP).

In step 63, the heart rate value 59 is transmitted from remote device 35 using the TCP communication protocol and is received onto local device 37. Compared to the encoded video data 56, the heart rate values 59 consist of less data and can be transmitted using a communication protocol such as TCP that guarantees information integrity. If a packet comprising the heart rate values is lost, that packet is retransmitted until its reception at local device 37 is acknowledged. So the heart rate values 59 will be reliably received at local device 37 even if some of the digital images of the video data 56 that were captured during the time interval are lost in transmission and are not resent under the UDP protocol.

In step 64, audio data is generated on remote device 35. The audio input is captured by microphone 45, which in this embodiment is the microphone of the patient's smartphone. In one example, the audio data is a stereo 2-channel (16 bit/channel) uncompressed data stream transmitted at 48 kHz, which corresponds to about 192 kBytes/sec. The audio data captures sounds spoken by patient 36. The raw audio data is then timestamped by timestamp module 46 before being received by speech-to-text converter 48. The time-stamped audio data is also compressed and encoded by compression encoding module 47 to generate encoded audio data 57 with timestamps, which is transmitted to local device 37. The speech-to-text converter 48 converts the audio data into words of text. The raw audio data that is converted into a particular word of text was captured starting at the first time instant, which corresponds to the time at which the intermediate image was captured. The intermediate image is the last image used to determine the heart beat length and thereby the instantaneous heart rate. For example, if the particular word spoken by patient 36 at the first time instant was "stressed", then the instantaneous heart rate of patient 36 at the moment the word "stressed" was spoken was 60 bpm.

In step 65, the particular word of text 58 is transmitted from remote device 35 using the TCP communication protocol and is received onto local device 37. As with the heart rate value 59, the particular word of text 58 is also reliably received at local device 37 even if some of the digital images of the video data 56 that were captured during the time interval (such as the intermediate image) are lost in transmission and are not resent under the UDP protocol.

In step 66, the particular word of text is displayed on the graphical user interface 50 of the local device 37 in association with an indication of the heart rate value. In one embodiment, the heart rate value is displayed below the word that was spoken at the time that patient 36 exhibited the displayed instantaneous heart rate, which was at the first time instant.

Figure 12:
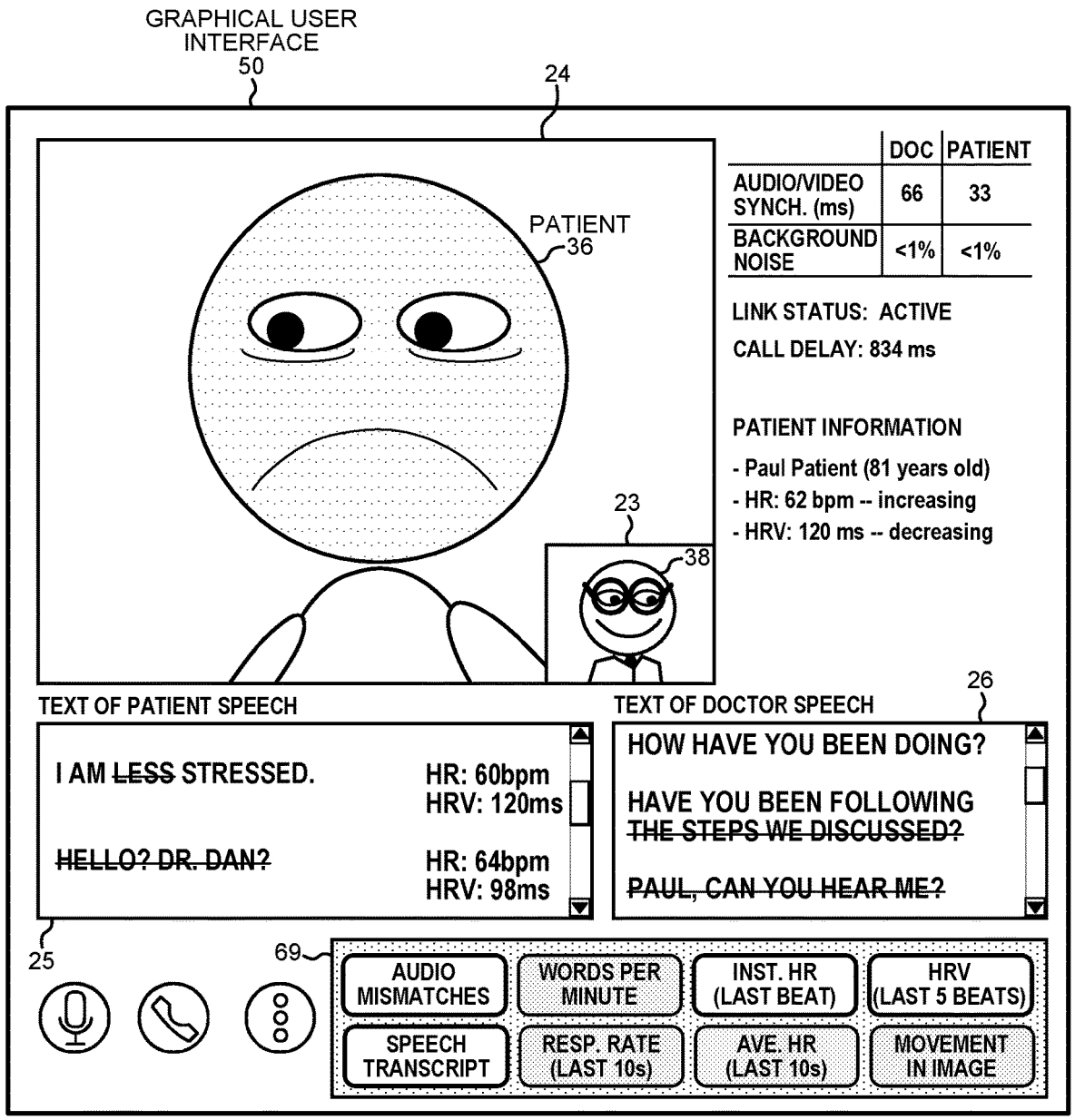
FIG. 12 shows an exemplary graphical user interface on which a transcribed word of a remote patient and an indication of the patient's heart rate are displayed in association with one another.

FIG. 12 shows graphical user interface 50 of local device 37 on which the particular word of text (in this example "stressed") and an indication of the heart rate value (in this example 60 bpm) are displayed in association with one another. In the embodiment of FIG. 12, the instantaneous heart rate (60 bpm) of patient 36 is displayed to the right of the phrase containing the word "stressed" in the panel 25, which indicates the acoustic output that health professional 38 (Dr. Dan) has actually received based on the speech signals from patient 36 (Paul Patient). From panel 25, it is apparent that the patient's instantaneous heart rate increases from 60 bpm to 64 bpm when the patient notices that the video conference has been interrupted, and the patient does not hear the conclusion of Dr. Dan's question "Have you been following . . . ?" Panel 25 indicates that patient 36 has an instantaneous heart rate of 64 bpm and a heart rate variability of 98 ms at the time that patient 36 spoke the words "Hello? Dr. Dan?" (which were never received by health professional 38).

The transcribed text shown in panel 26 provides a comparison of the speech of health professional 38 at the local device 37 and the speech that is output to patient 36 at remote device 35. Words of text presented with a strikethrough are words that were spoken by health professional 38 but that were not output to patient 36. In this example, health professional 38 (Dr. Dan) is able to determine whether the words he has spoken were accurately output to patient Paul by remote device 35. In the example of FIG. 12, panel 26 indicates that health professional 38 stated, "Have you been following the steps we discussed?", but only the phrase "Have you been following" was output to patient Paul. The words "the steps we discussed" were lost during transmission and were not played to patient 36. Thus, the words "the steps we discussed" are displayed with a strikethrough.

Panel 69 at the bottom of graphical user interface 50 includes various feature buttons that can be selected to display the corresponding feature to health professional 38. In this example, Dr. Dan has selected to be shown (1) audio mismatches, (2) a speech transcript, (3) the instantaneous heart rate, and (4) the heart rate variability. The instantaneous heart rate is displayed to the right of the phrase that includes the word spoken at the time that patient 36 exhibited the indicated instantaneous heart rate. Although there is some delay in determining the heart rate value, and the transcribed text can be transmitted to local device 37 sooner than can the heart rate value, the heart rate value is inserted to the right of the associated word in panel 25 as soon as the heart rate value is received onto local device 37. The video display controller 54 inserts the feature value to the right of the word that was spoken by patient 36 at the time the feature was determined based on the timestamps of the audio data and video data. Panel 69 indicates that the heart rate variability is calculated based on the variability of the length in milliseconds of the last five heart beats. For each feature determined by the feature extraction unit 42, there is a separate software module to perform the required calculations. The module for determining the heart rate variability is not shown in FIG. 9.

Panel 69 in FIG. 12 also shows that the system can determine and display for health professional 38 the words minute spoken by patient 36, the respiration (breathing) rate of patient 36 over the prior ten seconds, the average heart rate of patient 36 over the prior ten seconds, and the degree of movement in the video images of patient 36.

Figure 13:
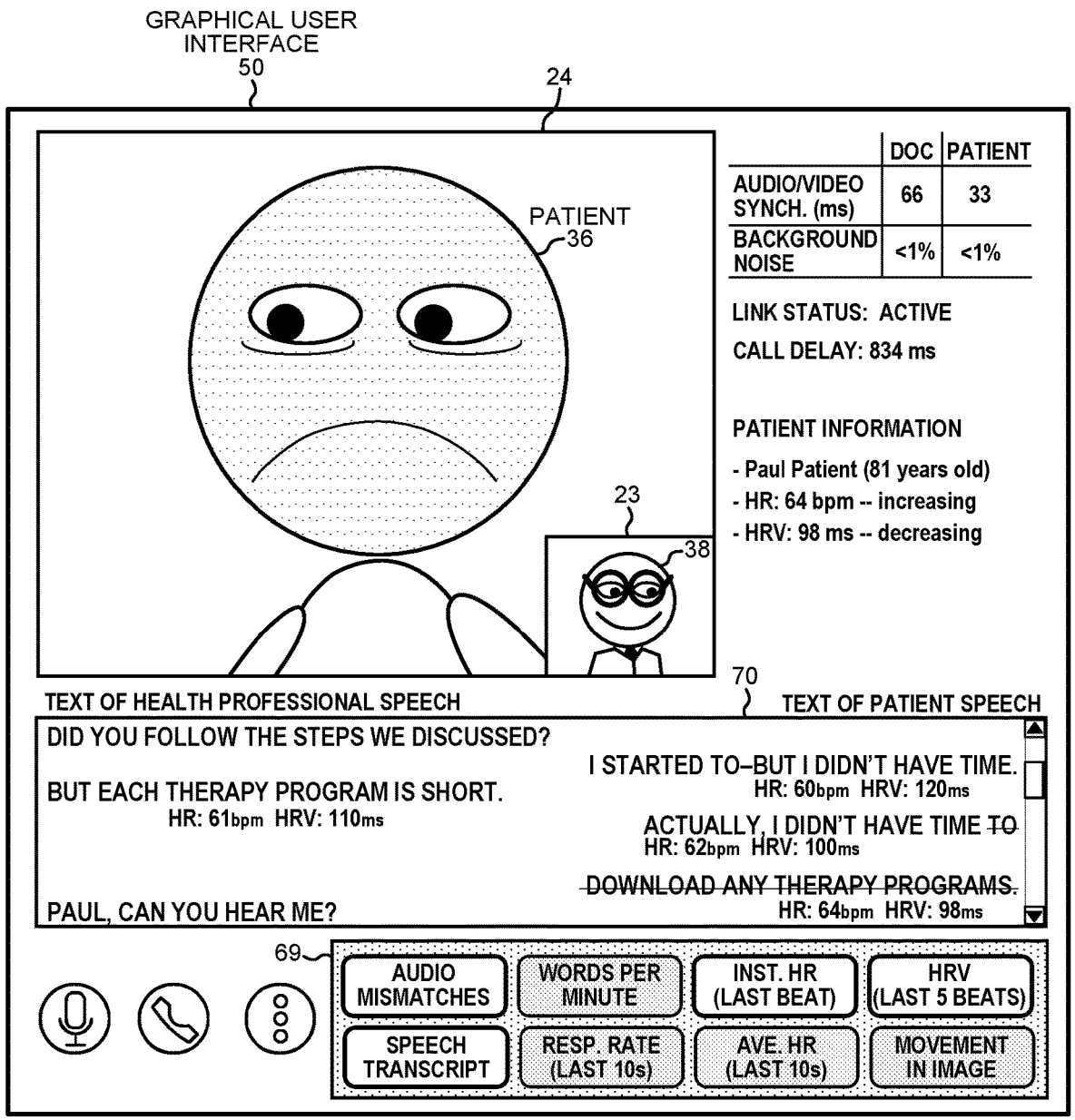
FIG. 13 shows another embodiment of how an indication of the patient's heart rate value and a concurrently spoken transcribed word are displayed in association with one another.

FIG. 13 shows another embodiment of how an indication of the patient's heart rate value and a concurrently spoken particular word of text are displayed in association with one another. In the embodiment of FIG. 13, the transcription of both the patient's and the health professional's speech is displayed in one larger panel 70. The particular word of text and the indication of the value of the patient's physiological feature are displayed in association with one another by displaying the value of the feature below the word that was spoken at the time instant when all of the data used to determine the value was acquired. The indications of the instantaneous heart rate and heart rate variability are displayed below the phrase that includes the word spoken at the time that patient 36 exhibited the indicated instantaneous heart rate and heart rate variability. For example, at the time instant that patient Paul 36 said the word "BUT", he had an instantaneous heart rate of 60 bpm and a heart rate variability of 120 ms. In addition, at the time instant that health professional 38 (Dr. Dan) said the word "THERAPY", patient Paul 36 had an instantaneous heart rate of 61 bpm and a heart rate variability of 110 ms.

In another aspect of the method 60 for conveying physiological parameters of remote patient 36 from remote device 35 to local device 37, a remote party combination feature is generated remotely by combining the remote party feature with an additional feature based on video data or audio data. The magnitude of the remote party combination feature is determined remotely at the location of the remote party. The remote party combination feature is determined based on the remote party feature combined with an additional feature that is based on the digital video data or on the audio data. The magnitude of the remote party combination feature is then received onto the local device. In one example, the additional feature is the level of background noise at the location of the remote party, which is determined using the audio data. The remote party feature is the heart rate of the remote party. This remote party combination feature can be used by health professional 38 to determine whether patient 36 is influenced by a stressful environment during the mental health therapy session.

In yet another embodiment of the novel method for monitoring aspects of a video conference, each video segment of a video tape is stored together with the associated value of a physiological parameter or feature characterizing the remote video participant at the time the video segment was captured. In one particular application, the remote party is a patient who is taking part in a mental health therapy session with a health professional. A distinct value of the physiological parameter is associated with each video segment of the overall video tape of the video conference. The method permits a large video tape of a mental health therapy session to be bookmarked at the locations during which the patient experienced higher levels of anxiety or arousal. The bookmarked video tape of the therapy session can later be retrieved from a database and more quickly reviewed by navigating directly to the most relevant video segments of the video tape.

Figure 14:
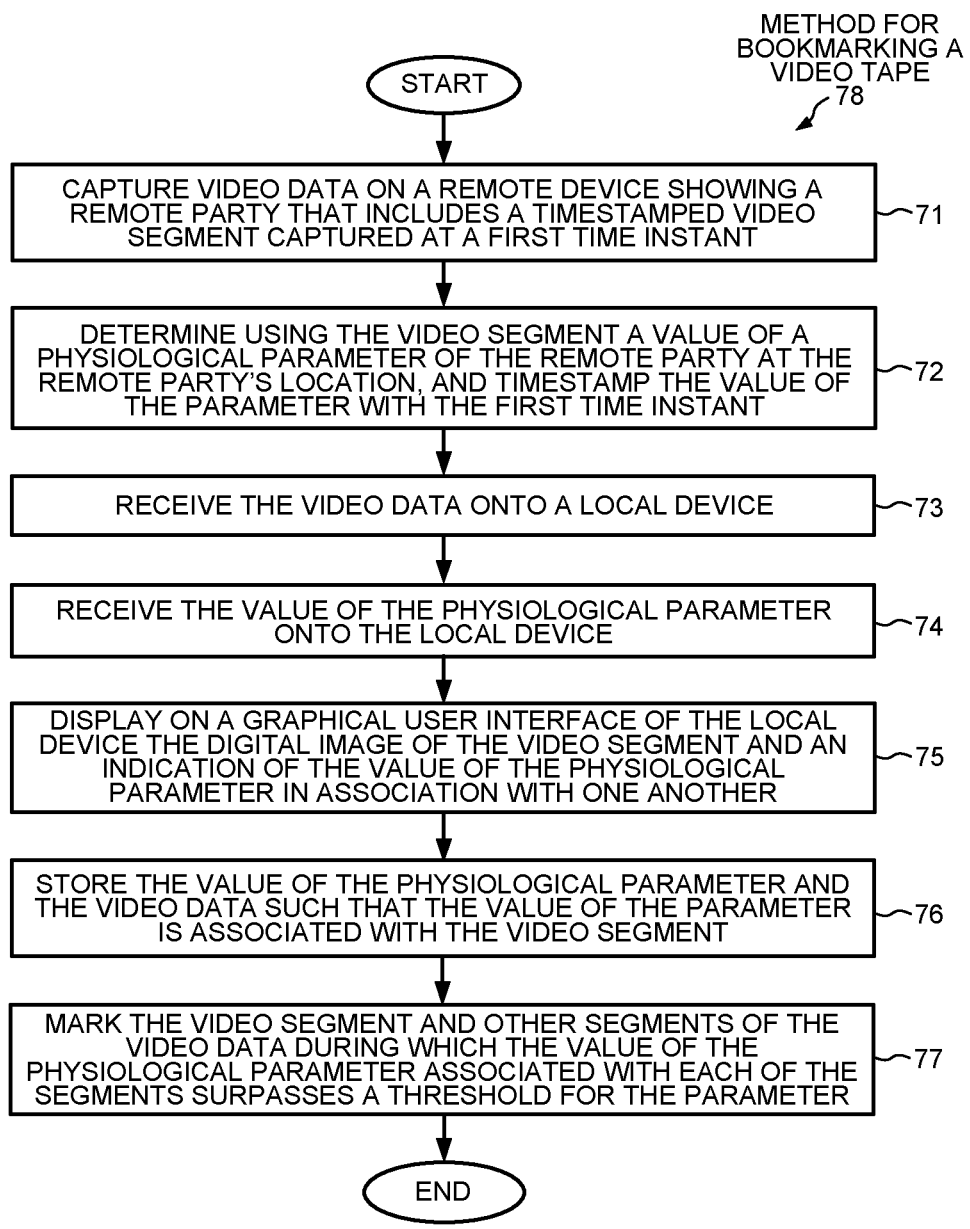
FIG. 14 is a flowchart of steps of a method for storing physiological parameter values of a remote party of a video conference together with the corresponding segment of the video tape at which the remote party exhibited the associated physiological characteristic.

FIG. 14 is a flowchart of steps 71-77 of a method 78 for storing physiological parameter values of a remote party of a video conference together with the corresponding segment of the video tape at which the remote party exhibited the associated physiological characteristic. For example, in one implementation the method stores the heart rate value of a remote patient in a mental health therapy session together with the video segment during which the patient exhibited the indicated heart rate. One application of the method is for bookmarking locations of a video tape during which a remote participant exhibited higher arousal or anxiety as indicated by the values of the physiological parameter at those locations in the video.

In a first step 71, video data showing a remote party is captured on a remote device. For example, the remote device 35 is the smartphone of patient 36, who is taking part in a mental health therapy session. The video data includes a video segment captured during a time interval. The video segment includes a digital image that was captured at a first time instant within the time interval. The digital image is timestamped with the first time instant. For example, the video data depicts patient 36 and shows a region of interest on the patient's forehead. A video segment of the video data has a length of about three seconds and includes about sixty-three digital images. One of the sixty-three digital images was captured at the first time instant, which coincides with the end of a single heart beat of the patient.

In step 72, the value of a physiological parameter of the remote party is determined using the video segment. The value of the physiological parameter is determined remotely at the location of the remote party. The value of the physiological parameter is timestamped with the first time instant. For example, the instantaneous heart rate value of patient 36 is determined remotely on remote device 35 and is timestamped with the time at which the digital image was captured, which coincides with the end of the heart beat from which the heart rate value was determined.

In step 73, the video data is received onto local device 37. The video data includes the video segment. For example, local device 37 is the laptop of health professional 38, who is administering a mental health therapy session to patient 36.

In step 74, the value of the physiological parameter is received onto local device 37. For example, the value of the physiological parameter is 64 bpm. The video segment and the value of the physiological parameter are not necessarily received onto local device 37 at the same time.

In step 75, the digital image of the video segment and an indication of the value of the physiological parameter are displayed in association with one another on the graphical user interface 50 of local device 37. Each timestamped value of the physiological parameter is associated with the video segment that includes the timestamped digital image that was timestamped with the same time instant. For example, the video segment (including the digital image) showing patient 36 as well as the heart rate value (64 bpm) are displayed in association with one another on the screen of the laptop of health professional 38. For example, the video segment showing patient 36 is displayed in panel 24, and the heart rate value 64 bpm is displayed in panel 25. The heart rate value 64 bpm is associated with a heart rate exhibited by patient 36 while the patient was being depicted by the video segment. Both the heart rate value and the digital image are timestamped with the first time instant.

In step 76, the value of the physiological parameter and the video data are stored such that the value of the physiological parameter is associated with the video segment. For example, the video data is forwarded by the local device 37 of health professional 38 to be stored in a database 78. In addition to viewing the video tape in real-time on the screen of his laptop, health professional 38 can also retrieve the video tape at a later time from database 78 to review the mental health therapy session with patient 36. The video data is stored such that each video segment of the video tape is associated with the value of the heart rate exhibited by patient 36 during that video segment. Because of how the video data and heart rate values are stored, health professional 38 can identify those video segments of the video tape during which patient 36 had a particular heart rate.

In step 77, a bookmarker module 79 in the local device 37 marks the video segment and other segments of the video data during which the value of the physiological parameter associated with each of the segments of the video data surpasses a threshold for the physiological parameter. For example, the video tape is bookmarked at locations at which the heart rate value of patient 36 exceeds a heart rate threshold, such as 90 bpm. This bookmarking allows health professional 38 to skip to those video segments of the video tape during which patient 36 exhibited high levels of anxiety or arousal. Health professional 38 can review the video of the therapy session in less time by skipping to the sections of the video that are most revealing about the patient's mental state.

In another embodiment, instead of a physiological parameter being stored in association with a video segment of a video tape, prosodic information is stored with the associated video segment from which the prosodic information was determined. The video tape can then be bookmarked at locations at which the patient 36 exhibits a particular emotion as indicated by the prosodic information. This type of bookmarking allows health professional 38 to skip to those video segments of the video tape during which patient 36 was, for example, angry, ironic or defensive.

In another application of the method, the heart rate values of a remote deponent in a litigation deposition are stored together with the video segment of the deposition during which the deponent exhibited the indicated heart rate. The locations in a deposition video tape are bookmarked during which the deponent exhibited higher arousal or anxiety as indicated by the deponent's heart rate values at those locations in the deposition. Alternatively, the video tape can be bookmarked based on prosodic information to indicate the locations in the deposition at which the deponent was, for example, defensive. An attorney reviewing a long deposition video tape can easily skip to the bookmarked segments during which the deponent was uncomfortable or defensive providing testimony on the questioned topic. The attorney can thereby review the video of the deposition in less time by skipping to the sections of the video that cover the testimony most likely to be contrary to the deponent's interests.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method comprising:
   receiving from a remote device, by one or more processors, digital video data captured during a time interval at a location of a remote party, wherein a digital image of the digital video data is captured at a first time instant within the time interval, and wherein the digital video data depicts the remote party;
   receiving from the remote device, by the one or more processors, a value of a remote party feature of the remote party, the value determined using the digital video data, wherein the value of the remote party feature is determined remotely at the location of the remote party;

receiving from the remote device, by the one or more processors, a particular word of text, wherein the remote device captures audio data comprising sounds spoken by the remote party, wherein the remote device converts the audio data into words of text, and wherein the audio data that is converted into a particular word of text was captured starting at the first time instant; and displaying on a graphical user interface, by the one or more processors, the digital video data, the particular word of text, and an indication of the value of the remote party feature in association with one another.

2. The method of claim 1, wherein the remote party feature is selected from the group consisting of: an instantaneous heart rate of the remote party at the first time instant, an average heart rate of the remote party over the time interval, a heart rate variability of heart beats of the remote party during the time interval, an average breathing rate of the remote party over the time interval, and an average pupil dilation amount of the remote party over the time interval.

3. The method of claim 1, wherein the remote party feature is indicative of high arousal of the remote party, and wherein the remote party feature is based on one or more physiological parameters selected from the group consisting of: an instantaneous heart rate of the remote party at the first time instant, an average heart rate of the remote party over the time interval, a heart rate variability of heart beats of the remote party during the time interval, an average breathing rate of the remote party over the time interval, and an average pupil dilation amount of the remote party over the time interval.

4. The method of claim 1, further comprising:
receiving, by the one or more processors, a magnitude of a remote party combination feature, wherein the remote party combination feature is determined based on the remote party feature combined with an additional feature, and wherein the additional feature is based on the digital video data or the audio data.

5. The method of claim 4, wherein the additional feature is a level of background noise at the location of the remote party determined using the audio data, and wherein the remote party feature is the heart rate of the remote party.

6. The method of claim 1, wherein the audio data captures background noise at the location of the remote party, further comprising:
receiving from the remote device, by the one or more processors, a value of the background noise; and
determining, by the one or more processors, a magnitude of a remote party combination feature, wherein the remote party combination feature is determined based on the remote party feature combined with the value of the background noise.

7. The method of claim 1, wherein the digital video data, the particular word of text, and the indication of the value of the remote party feature are displayed to a health professional, and wherein the remote party is a patient.

8. The method of claim 1, wherein the audio data captures ambient noise surrounding the remote party during the time interval, further comprising:
receiving from the remote device, by the one or more processors, an ambient noise value indicative of a magnitude of the ambient noise at the first time instant; and
displaying on the graphical user interface, by the one or more processors, the particular word of text, the indication of the value of the remote party feature, and the ambient noise value in association with each other.

9. The method of claim 1, further comprising:
storing, by the one or more processors, the audio data without storing any personal identifiable information of the remote party together with or linked to the audio data and without storing the digital video data together with or linked to the audio data.

10. The method of claim 9, wherein the personal identifiable information is information selected from the group consisting of: a name of the remote party, a date of birth of the remote party, a mailing address of the remote party, a residence address of the remote party, a phone number of the remote party, a driver's license number of the remote party, a Social Security Number of the remote party, a credit card number of the remote party, and a bank account number of the remote party.

11. The method of claim 1, further comprising:
detecting, by the one or more processors, that a telecommunications connection over which words of text were received from the remote device has been disconnected; and
requesting to the remote device, by the one or more processors, retransmission of the words of text that were converted from the audio data and that the remote device attempted to transmit while the telecommunications connection was disconnected.

12. The method of claim 1, wherein the remote device is a smartphone, and wherein the video data is captured by a camera of the smartphone.

13. The method of claim 1, wherein the digital video data, the particular word of text, and the indication of the value of the remote party feature are displayed to an attorney, and wherein the remote party is a deponent.

14. The method of claim 1, wherein the digital video data, the particular word of text, and the indication of the value of the remote party feature are displayed to a teacher, and wherein the remote party is a student.

* * * * *